US012637623B2

(12) United States Patent
Ojala et al.

(10) Patent No.: US 12,637,623 B2
(45) Date of Patent: May 26, 2026

(54) METHOD FOR UPGRADING BIO-BASED MATERIAL AND UPGRADED MATERIAL

(71) Applicant: Neste Oyj, Espoo (FI)

(72) Inventors: Antti Ojala, Porvoo (FI); Jukka Myllyoja, Porvoo (FI); Jaana Makkonen, Porvoo (FI); Rogier Van De Velde, Porvoo (FI); John Jamieson, Porvoo (FI)

(73) Assignee: NESTE OYJ, Espoo (FI)

( * ) Notice: Subject to any disclaimer, the term of this patent is extended or adjusted under 35 U.S.C. 154(b) by 847 days.

(21) Appl. No.: 17/782,228

(22) PCT Filed: Nov. 26, 2020

(86) PCT No.: PCT/EP2020/083466
§ 371 (c)(1),
(2) Date: Jun. 3, 2022

(87) PCT Pub. No.: WO2021/110524
PCT Pub. Date: Jun. 10, 2021

(65) Prior Publication Data
US 2023/0020748 A1 Jan. 19, 2023

(30) Foreign Application Priority Data

Dec. 6, 2019 (FI) ...................................... 20196063

(51) Int. Cl.
*C08F 210/06* (2006.01)
*B01D 53/14* (2006.01)
(Continued)

(52) U.S. Cl.
CPC ........... *C10G 3/50* (2013.01); *B01D 53/1462* (2013.01); *B01D 53/229* (2013.01); *C07C 1/22* (2013.01);
(Continued)

(58) Field of Classification Search
CPC .... B01D 2252/204; B01D 2252/20447; B01D 2256/16; B01D 2256/24; B01D 2257/304;
(Continued)

(56) References Cited

U.S. PATENT DOCUMENTS 8,546,626 B2 10/2013 Daudin et al.
8,795,392 B2 8/2014 Brevoord et al.
(Continued)

FOREIGN PATENT DOCUMENTS

CN 108440232 A * 8/2018 ............... C09C 1/50
EP 0591224 B1 2/1998
(Continued)

OTHER PUBLICATIONS

CN108440232A Description English (Year: 2018).*
(Continued)

*Primary Examiner* — Ellen M Mcavoy
*Assistant Examiner* — Chantel Graham
(74) *Attorney, Agent, or Firm* — Buchanan Ingersoll & Rooney PC

(57) ABSTRACT

Provided is a method for upgrading a bio-based material, the method including the steps of pre-treating bio-renewable oil(s) and/or fat(s) to provide a bio-based fresh feed material, hydrotreating the bio-based fresh feed material, followed by separation, to provide a bio-propane composition.

12 Claims, 2 Drawing Sheets

(51) Int. Cl.

| *B01D 53/22* | (2006.01) |
|---|---|
| *C07C 1/22* | (2006.01) |
| *C07C 5/27* | (2006.01) |
| *C07C 5/333* | (2006.01) |
| *C07C 7/00* | (2006.01) |
| *C07C 7/11* | (2006.01) |
| *C07C 7/144* | (2006.01) |
| *C10G 3/00* | (2006.01) |
| *C10G 65/02* | (2006.01) |

(52) U.S. Cl.
CPC .......... *C07C 5/2724* (2013.01); *C07C 5/3337* (2013.01); *C07C 7/005* (2013.01); *C07C 7/11* (2013.01); *C07C 7/144* (2013.01); *C08F 210/06* (2013.01); *C10G 3/44* (2013.01); *C10G 65/02* (2013.01); *B01D 2252/20447* (2013.01); *C10G 2300/1014* (2013.01); *C10G 2300/1018* (2013.01); *C10G 2300/202* (2013.01); *C10G 2300/205* (2013.01); *C10G 2300/207* (2013.01); *C10G 2300/4081* (2013.01); *C10G 2400/04* (2013.01); *C10G 2400/08* (2013.01)

(58) Field of Classification Search
CPC .............. B01D 2257/50; B01D 53/002; B01D 53/1462; B01D 53/229; C07C 1/22; C07C 11/06; C07C 5/2724; C07C 5/3337; C07C 7/005; C07C 7/11; C07C 7/144; C07C 9/08; C08F 210/06; C10G 2300/1007; C10G 2300/1011; C10G 2300/1014; C10G 2300/1018; C10G 2300/202; C10G 2300/205; C10G 2300/207; C10G 2300/4081; C10G 2400/04; C10G 2400/06; C10G 2400/08; C10G 2400/28; C10G 3/44; C10G 3/46; C10G 3/50; C10G 57/02; C10G 65/02; C10G 69/00; C10G 70/00; C11B 3/00; Y02P 20/151; Y02P 30/20
See application file for complete search history.

(56) References Cited

U.S. PATENT DOCUMENTS

| 9,556,089 B2 | 1/2017 | Kawakami et al. |
|---|---|---|
| 9,822,197 B2 | 11/2017 | Hörner et al. |
| 2003/0191351 A1 | 10/2003 | Voskoboynikov et al. |
| 2007/0010682 A1 | 1/2007 | Myllyoja et al. |
| 2009/0077868 A1 | 3/2009 | Brady et al. |
| 2009/0250379 A1 | 10/2009 | Kurtz et al. |
| 2009/0253947 A1 | 10/2009 | Brandvold et al. |
| 2010/0043278 A1 | 2/2010 | Brevoord et al. |
| 2010/0163458 A1 | 7/2010 | Daudin et al. |
| 2010/0331502 A1 | 12/2010 | Hecker et al. |
| 2011/0230632 A1 | 9/2011 | Abhari |
| 2014/0343341 A1 | 11/2014 | Kawakami et al. |
| 2015/0259265 A1 | 9/2015 | Fridman et al. |
| 2017/0081262 A1 | 3/2017 | Savolainen et al. |
| 2018/0119036 A1 | 5/2018 | Mani et al. |

FOREIGN PATENT DOCUMENTS

| EP | 1028985 B1 | 4/2003 | |
|---|---|---|---|
| EP | 2290034 A1 | 3/2011 | |
| EP | 2290035 A1 | 3/2011 | |
| EP | 2679656 A1 | 1/2014 | |
| JP | 2009540037 A | 11/2009 | |
| JP | 2013129606 A | 7/2013 | |
| JP | 2014224262 A | 12/2014 | |
| JP | 2018083866 A | 5/2018 | |
| WO | 9924478 A1 | 5/1999 | |
| WO | 9924479 A1 | 5/1999 | |
| WO | 0068315 A1 | 11/2000 | |
| WO | 03004808 A1 | 1/2003 | |
| WO | 2007003708 A1 | 1/2007 | |
| WO | WO-2011012440 A2 * | 2/2011 | .............. C10G 3/40 |
| WO | 2014079785 A2 | 5/2014 | |
| WO | 2014167181 A1 | 10/2014 | |
| WO | 2015004329 A1 | 1/2015 | |
| WO | 2016023973 A1 | 2/2016 | |
| WO | WO-2017045791 A1 * | 3/2017 | ............. F25J 3/0247 |
| WO | 2018052437 A1 | 3/2018 | |

OTHER PUBLICATIONS

Office Action issued Jan. 31, 2023, by the Canadian Intellectual Property Office in corresponding Canadian Patent Application No. 3,155,563. (4 pages).

Office Action issued on Jan. 24, 2024, by the Brazilian Patent Office in corresponding Brazilian Patent Application No. BR112022006058-0, and an English Translation of the Office Action. (8 pages).

Office Action (Notice of Reasons for Refusal) issued on Jul. 18, 2023, by the Japanese Patent Office in corresponding Japanese Patent Application No. 2022-533653, and an English Translation of the Office Action. (7 pages).

Office Action issued on Jul. 25, 2023, by the Canadian Patent Office in corresponding Canadian Patent Application No. 3,119,813. (7 pages).

Office Action (Decision of Refusal) issued on Oct. 31, 2023, by the Japanese Patent Office in corresponding Japanese Patent Application No. 2022-533653, and an English Translation of the Office Action. (6 pages).

Office Action issued on Oct. 25, 2024, by the Korean Patent Office in corresponding Korean Patent Application No. 10-2022-7014391, and an English Translation of the Office Action. (23 pages).

Office Action (Written Opinion) issued on Feb. 26, 2025, by the Singaporean Patent Office in corresponding Singaporean Patent Application No. 11202204401W. (8 pages).

Office Action issued on Apr. 12, 2024, by the Brazilian Patent Office in corresponding Brazilian Patent Application No. BR112022006058-0, and a machine English Translation of the Office Action. (24 pages).

Office Action issued on Apr. 2, 2024, by the Japanese Patent Office in corresponding Japanese Patent Application No. 2022-533653, and a machine English Translation of the Office Action. (5 pages).

Office Action issued on Apr. 30, 2024, by the Chinese Patent Office in corresponding Chinese Patent Application No. 202080083644.5, and a machine English Translation of the Office Action. (23 pages).

Office Action issued on Apr. 8, 2024, by the Canadian Patent Office in corresponding Canadian Patent Application No. 3,155,563. (1 page).

Office Action issued on Sep. 26, 2023, by the Chinese Patent Office in corresponding Chinese Patent Application No. 202080083644.5. (10 pages).

International Search Report (PCT/ISA/210) and Written Opinion (PCT/ISA/237) mailed on Feb. 24, 2021, by the European Patent Office as the International Searching Authority for International Application No. PCT/EP2020/083466. (12 pages).

Office Action and Search Report mailed on Apr. 3, 2020 issued in corresponding Finnish U.S. Appl. No. 20/196,063 by the Finnish Patent and Registration Office. (8 pages).

International Preliminary Report on Patentability and Written Opinion of the International Searching Authority (Forms PCT/IB/373 and PCT/ISA/237) issued on May 17, 2022, by the International Bureau of WIPO, in corresponding International Application No. PCT/EP2020/083466. (8 pages).

Office Action (Notice of Final Rejection) issued on Jul. 23, 2025, by the Korean Patent Office in corresponding Korean Patent Application No. 10-2022-7014391, and an English Translation of the Office Action. (10 pages).

(56) References Cited

OTHER PUBLICATIONS

Office Action (Communication) issued on Aug. 14, 2025, by the European Patent Office in corresponding European Patent Application No. 20 816 426.9. (8 pages).

* cited by examiner

FIG. 1

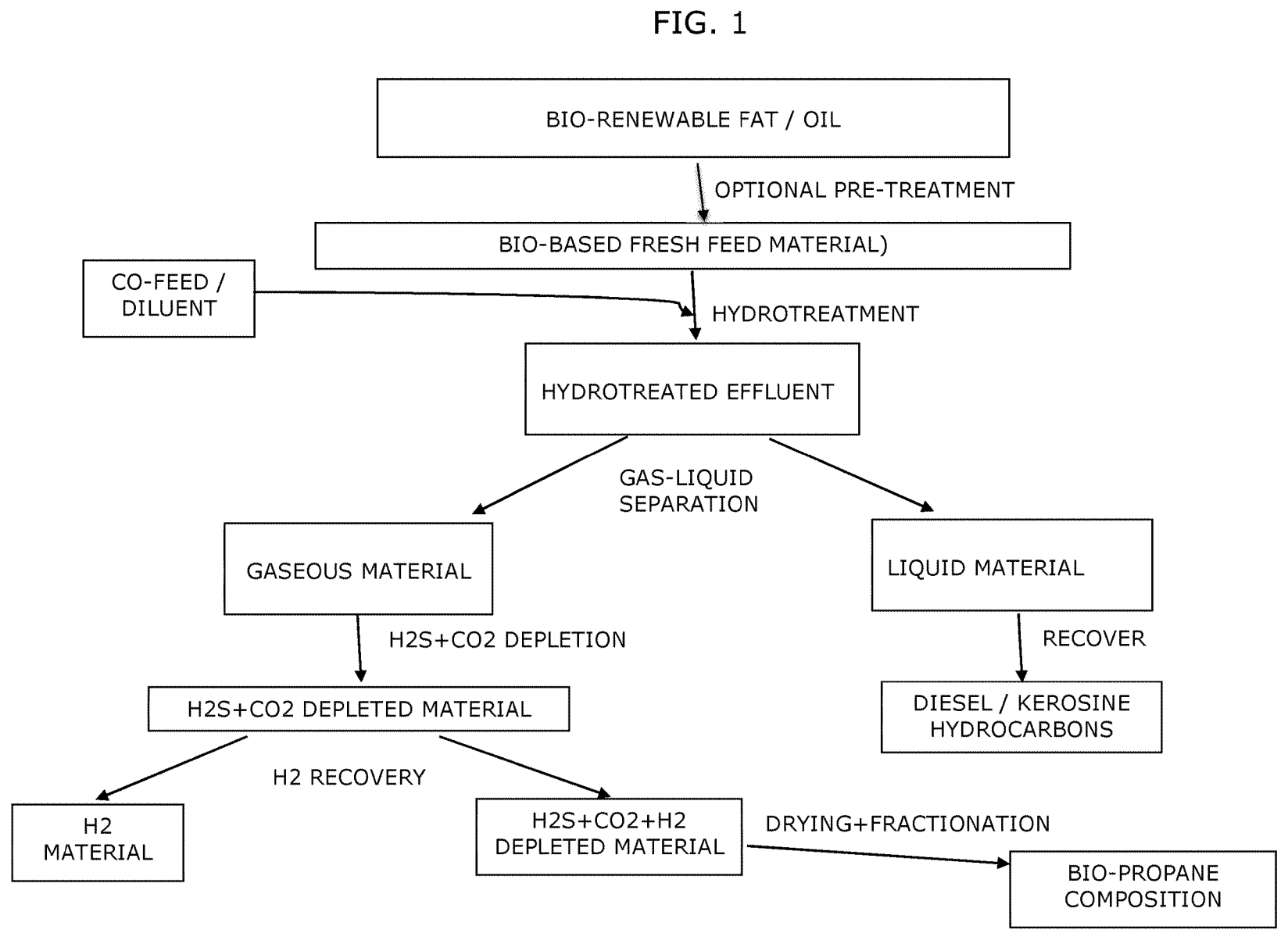

BIO-RENEWABLE FAT / OIL

OPTIONAL PRE-TREATMENT

BIO-BASED FRESH FEED MATERIAL)

CO-FEED / DILUENT

HYDROTREATMENT

HYDROTREATED EFFLUENT

GAS-LIQUID SEPARATION

LIQUID MATERIAL

RECOVER

DIESEL / KEROSINE HYDROCARBONS

GASEOUS MATERIAL

H2S+CO2 DEPLETION

H2S+CO2 DEPLETED MATERIAL

H2 RECOVERY

H2 MATERIAL

H2S+CO2+H2 DEPLETED MATERIAL

DRYING+FRACTIONATION

BIO-PROPANE COMPOSITION

FIG. 2

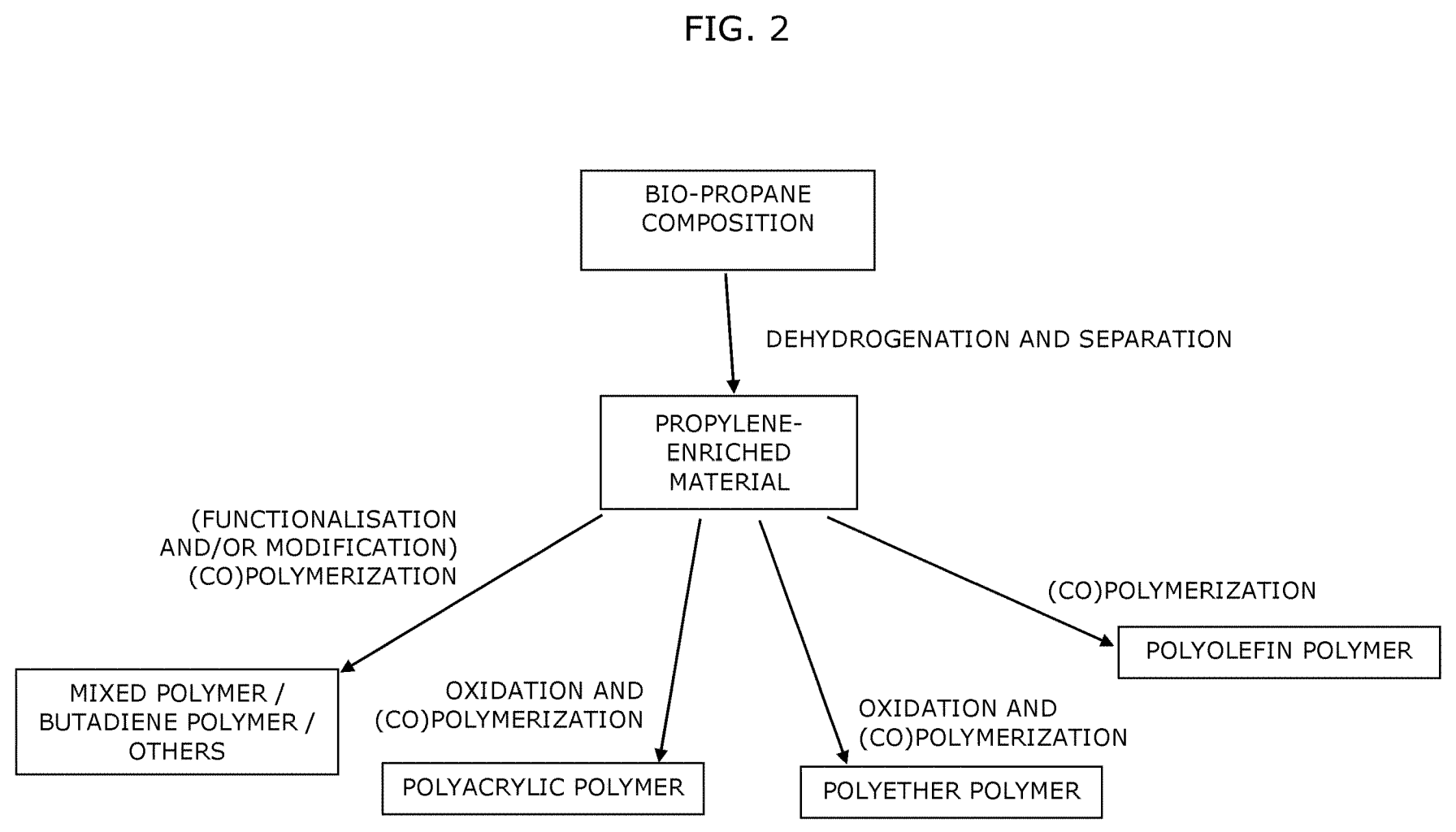

BIO-PROPANE COMPOSITION

DEHYDROGENATION AND SEPARATION

PROPYLENE-ENRICHED MATERIAL (CO)POLYMERIZATION

POLYOLEFIN POLYMER

OXIDATION AND (CO)POLYMERIZATION

POLYETHER POLYMER

OXIDATION AND (CO)POLYMERIZATION

POLYACRYLIC POLYMER (FUNCTIONALISATION AND/OR MODIFICATION) (CO)POLYMERIZATION

MIXED POLYMER / BUTADIENE POLYMER / OTHERS

METHOD FOR UPGRADING BIO-BASED MATERIAL AND UPGRADED MATERIAL

TECHNICAL FIELD

The present invention relates to a method for upgrading bio-based material into valuable bio-based products. Specifically, the present invention relates to a method for producing bio-propane from oil(s) and/or fat(s). The invention further relates to upgraded material obtainable by upgrading bio-based material. More specifically, the present invention relates to a method of subjecting naturally occurring (renewable; bio-based) oils(s) and/or fat(s) to hydrogenation, purifying the hydrotreated material and separating a bio-propane composition. The bio-propane composition may then be further processed (upgraded) to bio-monomers or bio-polymers.

TECHNICAL BACKGROUND

In the recent years, sustainability of chemical processes has become an increasing issue. All over the world, efforts are being made to replace conventional (fossil) materials with renewable (bio-based) materials.

Propane is one of the chemicals which was traditionally produced from crude oil by distillation or in the course of the value-added chain of processing crude oil (e.g. as a side product in cracking reactions). The techniques for producing propane from fossil sources are well established. Furthermore, these processes cannot be easily transferred to renewable materials because such materials usually contain significant amounts of oxygenates (oxygen-containing organic compounds) having a carbon number distribution which significantly differs from the carbon number distribution of crude oil. Some success has been achieved to produce bio-based fuel components e.g. in the diesel or gasoline range.

Bio-renewable oil(s) and fat(s) comprise glycerides, and every glyceride molecule (e.g. mono-, di-, triglyceridic) contains a glycerol backbone. Upon hydrogenation, this glycerol backbone is usually converted into bio-propane. This bio-propane is currently marketed as a fuel.

Propylene, on the other hand, is a base material for several high volume chemicals such as acrylic acid, propylene oxide and polypropylene that are consumed annually about 2700 kt, 9000 kt and 60 000 kt, respectively. Acrylic acids are mainly used in the production of super absorbents, coatings and paints. Propylene oxide is as precursor for several high volume chemicals such as butanediol, polyether polyol and propylene glycol. Polypropylene (PP) is the second most common thermoplastic polymer and it is found in many applications such as packages, transportation, construction, consumer goods, electronics etc.

The majority of the propylene production at present is based on fossil material and involves large scale cracking facilities.

Presently available methods to produce bio-based polypropylene, propylene oxide or acrylic acid have only limited value for industrial scale production.

WO 2014/079785 A1 discloses a method for producing water absorbent polymer particles comprising thermal cracking/steam cracking e.g. oils/fats ("bio-naphtha") to produce a mixture comprising propane and propylene, gas phase oxidation of the mixture to form acrylic acid and propionic acid, and subsequent polymerization.

WO 2017/045791 A1 discloses a process for separation and purification of renewable propane.

EP 2 290 034 A1 discloses a method of steam-cracking free fatty acids (FFA) and/or fats/oils to produce mainly propylene and ethylene.

US 2011/0230632 A1 discloses a method for conversion of biomass to polymers, including steam cracking of hydrocarbons derived from biomass and subsequent polymerization of olefins obtained by steam cracking.

SUMMARY OF THE INVENTION

Manufacturing paraffinic liquid hydrocarbons by subjecting a bio-based fresh feed material of bio-renewable oil(s) and/or fat(s) comprising glycerol-equivalent moieties to a hydrotreatment on a sulphided metal catalyst involves generation of high amounts of gaseous reaction products.

Examples of these gaseous reaction products may include $H_2O$ cleaved by hydrotreatment (HDO) from the organic oxygenates present in the bio-based fresh feed material; CO and $CO_2$ cleaved by decarbonylation and decarboxylation (in the following sometimes simply referred to as decarb reactions) of C3+ organic oxygenates (oxygenates having more than 3 carbon atoms) such as fatty acids contained in the bio-based fresh feed; propane, originating mainly from the glycerol-equivalent moieties; cracking products of organic oxygenates such as fatty acids or hydrocarbons obtained therefrom or used for diluting the fresh feed; $H_2S$ cleaved by hydrodesulphurization from organic Sulphur containing compounds present in some bio-based fresh feed materials and/or added for maintaining the hydrotreatment (HDO) catalyst in sulphided form; and $NH_3$ cleaved by hydrodenitrogenation from organic nitrogen containing compounds typically present in the bio-based fresh feed material. Additionally the gaseous hydrotreated material may comprise significant amounts of unused (unreacted) hydrogen ($H_2$).

Typically full deoxygenation of the bio-based fresh feed material is desired so as to achieve high quality paraffinic hydrocarbon products meeting e.g. stringent specifications for diesel fuel and aviation grade kerosene. This may require high amounts of (expensive) $H_2$ raising concerns of process economy. Therefore, conventionally, the occurrence of decarb reactions was regarded as being rather beneficial when processing a bio-based fresh feed material. For example US 20070010682 A proposes running the deoxygenation using conditions favouring decarb-reactions over HDO thereby reducing $H_2$ consumption.

However decarb-reactions have the drawback of obtaining hydrocarbons with chain length reduced by one carbon atom which may reduce the yield of diesel and/or kerosene range hydrocarbons. Some authors have proposed converting light hydrocarbons contained in the gaseous effluent from the hydrotreatment reactor by steam reforming into $H_2$ and carbon oxides, and recycling the $H_2$ to HDO step (e.g. US 20090250376 A1), thus reducing the overall hydrogen consumption. However, this again involves breaking down valuable carbon-carbon bonds and further requires laborious purification of the $H_2$ before feeding into HDO reactor.

Additionally when decarb-reactions are favoured over HDO during deoxygenation, high amounts of carbon oxides are generated to the gaseous hydrotreated material, thus requiring separation and disposal. The higher the gaseous impurity level versus the bio-propane content in the gaseous hydrotreated material, the more laborious purification process is required for achieving sufficient purity so that the bio-propane composition could be used in high value applications, for example as a feed for catalytic processes such as for catalytic dehydrogenation into bio-propylene. Also compressing a bio-propane gas composition containing high impurity levels may be more challenging, and may involve e.g. higher energy consumption.

One further challenge involved with hydrotreatment (HDO) of bio-based materials using sulphided metal catalysts and decarb-favouring conditions is an increased risk of formation of carbonyl sulphide, COS. COS is found naturally in petroleum fractions, making it an issue in numerous petrochemical processes. Because propane and COS have similar boiling temperatures, even after separation (e.g. by distillation), roughly 90% of the petrochemical COS is usually found in the propane fraction.

Bio-based samples do not initially contain COS. However, COS is generated when $CO_2$ reacts with $H_2S$ yielding COS and $H_2O$, according to the following equilibrium equation:

$$CO_2+H_2S \leftrightarrow COS+H_2O. \tag{1}$$

COS that has ended up in the propane composition, may thus undergo hydrolysis to yield $CO_2$ and $H_2S$. Both $H_2S$ and COS may be troublesome contaminants for high value applications like catalytic conversion of the propane. Gaseous hydrotreated materials obtained by HDO of bio-based materials using sulphided metal catalysts and decarb-favouring conditions usually contain high amounts of $H_2S$ and $CO_2$, thus driving the equilibrium equation (1) towards COS. $H_2O$ present in the gaseous stream may help in keeping the equilibrium on left. However, also $H_2O$ is an undesired contaminant in bio-propane compositions.

The present invention is directed to an improved method for upgrading a bio-based material into valuable bio-based products. The method involves reduced cleavage of valuable carbon-carbon bonds in the bio-based fresh feed material resulting in higher yields of high quality liquid and gaseous hydrocarbon products, meeting stringent product specifications. This is achieved by the method according to the appended claims.

Specifically, it is an object of the present invention to provide an improved method for upgrading a bio-renewable fat(s) and/or oil(s). It is a further object to provide an upgraded material. It is an additional object to provide an improved method for the production of bio-propane, as well as a method of employing this bio-propane in the manufacturing process of a monomer material or a polymer material, and to provide a monomer material and/or a polymer material.

The present invention relates to one or more of the following items:

1. A method for upgrading a bio-based material, comprising the steps of:
   (A) providing a bio-based fresh feed material of bio-renewable oils and/or fats having a glycerol-equivalent content of 2 wt.-% to 60 wt.-% relative to the total weight of the bio-based fresh feed material;
   (B) subjecting a hydrotreatment feed comprising the bio-based fresh feed material and an optional diluent to a hydrotreatment comprising HDO in the presence of a sulphided metal catalyst and hydrogen ($H_2$), to provide a hydrotreated effluent, wherein the hydrotreatment feed comprises 10-10 000 wt.-ppm of Sulphur-containing compound calculated as elemental S;
   (C) subjecting the hydrotreated effluent to gas-liquid separation so as to provide a gaseous hydrotreated material comprising Hz, bio-propane, $H_2O$, $H_2S$, $CO_2$, and CO, and a liquid hydrotreated material comprising paraffinic hydrocarbons;

(D) subjecting the liquid hydrotreated material to fractionation, after an optional second hydrotreatment, and recovering at least diesel and/or kerosene range paraffinic hydrocarbon material;
   (E) subjecting the gaseous hydrotreated material to a purification step for removing $H_2S$ and $CO_2$ to obtain a $H_2S$ and $CO_2$ depleted gaseous stream;
   (F) subjecting the $H_2S$ and $CO_2$ depleted gaseous stream to $H_2$ recovering and drying to obtain dried $H_2S$, $CO_2$ and $H_2$ depleted gaseous stream;
   (G) fractionating the dried $H_2S$, $CO_2$ and $H_2$ depleted gaseous stream to recover a bio-propane gas composition, and optionally compressing the bio-propane gas composition to obtain a liquefied bio-propane composition.

The content of the sulphur in the hydrotreatment feed and/or in the bio-based fresh feed, calculated as elemental S, may be determined in accordance with EN ISO 20846.

2. The method according to item 1, wherein the bio-based fresh feed material has a glycerol-equivalent content of at least 3 wt. %, preferably at least 4 wt. %, more preferably at least 5 wt. %, even more preferably at least 6 wt. %, most preferably at least 7 wt. %, or at least 8 wt. %.

3. The method according to item 1 or 2, wherein the bio-based fresh feed material has a glycerol-equivalent content of 55 wt. % or less, preferably 50 wt. % or less, or 45 wt. % or less, or 40 wt.-% or less, or 35 wt. % or less, or 30 wt.-% or less, or 25 wt. % or less, or 20 w % or less; and/or the bio-based fresh feed material has a glycerol-equivalent content of 4 wt. % to 50 wt.-%, preferably 6 wt.-% to 40 wt.-%, or 7 wt.-% to 30 wt.-%.

4. The method according to any one of the preceding items, wherein the hydrotreatment feed comprises 10-1 000 wt.-ppm, preferably 10-500 wt.-ppm, more preferably 10-300 wt.-ppm, even more preferably 10-200 wt.-ppm, most preferably 20-100 wt.-ppm of Sulphur-containing compound calculated as elemental S.

5. The method according to any one of the preceding items, comprising, in step (D), subjecting the liquid hydrotreated material to fractionation after a second hydrotreatment comprising hydroisomerization, and recovering at least diesel and/or kerosene range iso-paraffinic hydrocarbon material, in particular diesel range iso-paraffinic hydrocarbon material meeting EN 590 requirements for automotive diesel fuel and/or kerosene range iso-paraffinic hydrocarbon material meeting ASTM D7566-16b, Annex A2, meeting requirements for aviation turbine fuel.

6. The method according to any one of the preceding items, comprising, in step (D), subjecting the liquid hydrotreated material to fractionation, and recovering at least diesel and/or kerosene range iso-paraffinic hydrocarbon material, in particular diesel range iso-paraffinic hydrocarbon material meeting EN 590 requirements for automotive diesel fuel and/or kerosene range iso-paraffinic hydrocarbon material meeting ASTM D7566-16b, Annex A2, meeting requirements for aviation turbine fuel; wherein the hydrotreatment in step (B) further comprises hydroisomerization.

7. The method according to any one of the preceding items, wherein the purification step (E) further comprises a step (E') of recovering the $H_2S$ removed from the gaseous hydrotreated material and recycling the recovered $H_2S$ to the hydrotreatment step (B).

In these embodiments such recycled $H_2S$ is calculated as being part of the specified range of sulphur-containing compound in the hydrotreatment feed (10-10 000 wt.-ppm, calculated as elemental S), and may be co-fed e.g. with the hydrogen and/or separately to the hydrotreatment step (B).

8. The method according to any one of the preceding items, wherein the bio-propane gas composition has a propane content of at least 90 wt.-%, at least 91 wt.-%, at least 92 wt.-%, at least 93 wt.-%, at least 94 wt.-%, at least 95 wt.-%, at least 96 wt.-%, or at least 97 wt.-%.

9. The method according to any one of the preceding items, wherein the liquefied bio-propane composition has a propane content of at least 90 wt.-%, at least 91 wt.-%, at least 92 wt.-%, at least 93 wt.-%, at least 94 wt.-%, at least 95 wt.-%, at least 96 wt.-%, or at least 97 wt.-%.

10. The method according to any one of the preceding items, further comprising a step of subjecting at least part of the bio-propane gas composition and/or the liquefied bio-propane composition to a conversion comprising catalytic dehydrogenation to obtain a dehydrogenation effluent, followed by recovering at least bio-propylene in the dehydrogenation effluent to obtain, after optional purification, a bio-propylene composition.

11. The method according to item 10, wherein the at least part of the bio-propane gas composition and/or the liquefied bio-propane composition is subjected to a conversion comprising catalytic dehydrogenation together with a fossil propane composition (gaseous or liquid) such that the total propane composition (liquid and/or gaseous) has a renewable content of at least 0.1 percent, preferably at least 0.5 percent, at least 1 percent, at least 2 percent, at least 5 percent, at least 10 percent, at least 20 percent, at least 40 percent, at least 50 percent, at least 75 percent, at least 90 percent, particularly preferably about 100 percent.

The renewable content is measureable by $^{14}C$ analysis (content of $^{14}C$ isotopes) as described below. The total propane composition refers to the total material of the bio-propane gas composition, the liquefied bio-propane composition, the fossil propane gas composition and the liquefied fossil propane composition which is subjected to the conversion. Preferably, the resulting bio-propylene composition has the same renewable content as mentioned as the total propane composition mentioned above.

12. The method according to item 10 or 11, further comprising (co)polymerizing at least bio-propylene of the bio-propylene composition and/or at least a derivative of bio-propylene of the bio-propylene composition, optionally together with other (co)monomer(s), to produce a bio-polymer.

The (co)polymerizing may involve also use of propylene or other (co)monomers of fossil origin. In this connection by bio-polymer it is meant that the obtained polymer has at least some biogenic carbon content, preferably at least 0.1 percent, preferably at least 0.5 percent, at least 1 percent, at least 2 percent, at least 5 percent, at least 10 percent, at least 20 percent, at least 40 percent, more preferably at least 50 percent, as measurable by $^{14}C$ analysis (ASTM D6866).

13. The method according to any one of the preceding items, wherein the step (A) comprises a step (A') of pre-treating bio-renewable oil(s) and/or fat(s) for reducing contaminants in the oil(s) and/or fat(s) to produce the bio-based fresh feed material.

14. The method according to item 13, wherein the pre-treatment step (A') is a step of reducing contaminants containing S, N and/or P in the oil(s) and/or fat(s) to produce the bio-based fresh feed material, and/or the pre-treatment step (A') is a step of reducing metal-containing contaminants in the oil(s) and/or fat(s) to produce the bio-based fresh feed material.

Preferably the pre-treatment step reduces content of one or more of alkali metals, alkaline earth metals, Si, Al, Fe, Zn, Cu, Mn, Cd, Pb, As, Cr, Ni, V, Sn.

15. The method according to item 13 or 14, wherein the pre-treatment step (A') comprises one or more selected from washing, degumming, bleaching, distillation, fractionation, rendering, heat treatment, evaporation, filtering, adsorption, hydrodeoxygenation, centrifugation or precipitation.

The above pre-treatment methods are simple and effective methods for removing the potentially catalyst-poisoning S, N and P contaminants as well as metal contaminants (metals and/or metal compounds), including metalloid contaminants, such as Si-containing impurities.

16. The method according to any one of items 13 to 15, wherein the step of pre-treatment of the bio-based fresh feed material comprises at least one of partial hydrogenation, partial deoxygenation, hydrolysis and transesterification.

17. The method according to any one of the preceding items, wherein the bio-based fresh feed material comprises glycerol and/or fatty acid esters of glycerol.

18. The method according to any one of the preceding items, wherein the bio-based fresh feed material comprises glycerol which is produced by hydrolysis and/or transesterification of the bio-renewable oil(s) and/or fat(s).

19. The method according to any one of the preceding items, wherein the fractionation step (G) comprises cryogenic fractionation and/or elevated pressure distillation.

20. The method according to any one of the preceding items, wherein the bio-based fresh feed material has a total sulphur content of at most 500 ppm, preferably at most 300 ppm, at most 200 ppm, at most 100 ppm, at most 60 ppm, at most 50 ppm, at most 40 ppm, at most 35 ppm, at most 30 ppm, at most 25 ppm, at most 20 ppm, at most 15 ppm, at most 10 ppm, or at most 5 ppm.

22. The method according to any one of the preceding items, wherein bio-based fresh feed material has a total phosphorus content of at most 300 ppm, preferably at most 200 ppm, at most 100 ppm, at most 80 ppm, at most 50 ppm, at most 40 ppm, at most 35 ppm, at most 30 ppm, at most 25 ppm, at most 20 ppm, at most 15 ppm, at most 10 ppm, or at most 5 ppm.

23. The method according to any one of the preceding items, wherein bio-based fresh feed material has a total nitrogen content of at most 400 ppm, preferably at most 300 ppm, at most 200 ppm, at most 100 ppm, at most 60 ppm, at most 40 ppm, at most 35 ppm, at most 30 ppm, at most 25 ppm, at most 20 ppm, at most 15 ppm, at most 10 ppm, or at most 5 ppm.

The contents of the above-mentioned contaminants can be reduced to considerably low amounts using comparatively simple procedures. This allows production of a bio-propane composition having low amounts of contaminants and thus being specifically suited for being upgraded to higher-value products.

Although the pre-treatment, if applied, is suited to remove most of the contaminants, it may be desirable to further remove such contaminants from the propane feed in order to achieve even higher purity.

24. The method according to any one of the preceding items, wherein the hydrotreatment feed in the hydrotreatment step (B) comprises a diluent comprising paraffinic hydrocarbons.

As explained in detail below, a diluent is particularly suited for temperature control during hydrotreatment, specifically during hydrodeoxygenation.

25. The method according to item 24, wherein the diluent comprises at least one of recycled paraffinic hydrocarbons from the hydrotreatment step, renewable hydrocarbons obtained by Fischer-Tropsch of bio-syngas, and fossil-based hydrocarbons.

26. The method according to item 24 or 25, wherein the diluent comprises recycled paraffinic hydrocarbons from the hydrotreatment step.

27. The method according to item 24, 25 or 26, wherein the hydrotreatment feed contains at least 2 wt.-% of the bio-based fresh feed material, preferably at least 3 wt.-%, at least 4 wt.-%, at least 5 wt.-%, at least 6 wt.-%, at least 7 wt.-%, at least 8 wt.-%, at least 9 wt.-%, at least 10 wt.-%, at least 11 wt.-%, at least 12 wt.-%, at least 15 wt.-%, at least 20 wt.-%, at least 25 wt.-%, at least 50 wt.-%, at least 75 wt.-%, at least 90 wt.-% or at least 95 wt.-%, or at least 99 wt.-%.

28. The method according to any one of items 24 to 27, wherein the hydrotreatment feed contains 99 wt.-% or less of a bio-based fresh feed material, preferably 90 wt.-% or less, 75 wt.-% or less, 50 wt.-% or less, 40 wt.-% or less, 35 wt.-% or less, 30 wt.-% or less, 25 wt.-% or less, 20 wt.-% or less, 15 wt.-% or less, or 10 wt.-% or less.

29. The method according to any one of items 24 to 28, wherein the diluent comprises recycled paraffinic hydrocarbons from the hydrotreatment step and the hydrotreatment feed contains at least 10 wt.-% of the recycled paraffinic hydrocarbons from the hydrotreatment step, preferably at least 25 wt.-%, at least 40 wt.-%, at least 50 wt.-%, at least 60 wt.-%, at least 70 wt.-%, at least 75 wt.-%, at least 80 wt.-%, at least 85 wt.-%, at least 90 wt.-%, or at least 92 wt.-%.

The recycled product from the hydrotreatment step is preferably a hydrocarbon, but may similarly be a material which is only partially deoxygenated.

30. The method according to any one of items 24 to 29, wherein the diluent comprises recycled paraffinic hydrocarbons from the hydrotreatment step and the hydrotreatment feed contains 98 wt.-% or less, 95 wt.-% or less, 92 wt.-% or less, 90 wt.-% or less, 85 wt.-% or less, 80 wt.-% or less, 70 wt.-% or less, 60 wt.-% or less, 40 wt.-% or less or 25 wt.-% or less of the recycled paraffinic hydrocarbons from the hydrotreatment step.

31. The method according to any one of the preceding items, wherein the fractionation step (G) comprises a step of separating at least bio-propane from heavier hydrocarbon products (C3+ hydrocarbons), preferably using a distillation or evaporation technique.

32. The method according to any one of the preceding items, wherein the H$_2$ recovering step (F) comprises separating at least hydrogen from the H$_2$S and CO$_2$ depleted gaseous stream using a membrane separation technique to obtain the H$_2$S, CO$_2$ and H$_2$ depleted gaseous stream.

33. A liquefied bio-propane composition having a vapour pressure of 1200-1500 kPa at 40° C. and a density of 495-520 kg/m$^3$ at 15° C., and comprising:
  at least 94 wt.-% of bio-propane;
  at most 2000 wt.-ppm of CO$_2$;
  at most 1000 wt-ppm of CO;
  at most 15 wt.-ppm of S-containing compounds, calculated as elemental S;
  at most 1500 wt.-ppm of unsaturated hydrocarbons;
  at most 5.5 wt.-% of hydrocarbons having more than 3 carbon atoms (C3+ hydrocarbons); whereof at most 1.4 wt.-% (relative to the liquefied bio-propane composition) are hydrocarbons having 5 or more carbon atoms.

The liquefied bio-propane composition may be a fully renewable bio-propane composition or may be a bio-propane composition which is a blend of a renewable and a fossil material. The liquefied bio-propane composition preferably has a biogenic carbon content (as described below) of at least 5 percent, more preferably at least 10 percent, at least 50 percent, at least 75 percent, at least 90 percent or about 100 percent.

34. The liquefied bio-propane composition according to item 33,
  having a vapour pressure of 1250-1450 kPa, preferably 1300-1430 kPa, at 40° C.; and/or
  having a density of 500-515 kg/m$^3$, more preferably 500-510 kg/m$^3$, at 15° C.; and/or
  comprising at least 95 wt.-% of bio-propane, preferably at least 96 w % of bio-propane; and/or
  comprising at most 1800 wt.-ppm, preferably at most 1500 wt.-ppm, more preferably at most 1000 wt.-ppm, even more preferably at most 500 wt.-ppm of CO$_2$ (carbon dioxide); and/or
  comprising at most 500 wt.-ppm of CO, preferably at most 100 wt.-ppm, more preferably at most 50 wt.-ppm of CO (carbon monoxide).

The content of CO$_2$ may be determined in accordance with ASTM D 2505. The content of CO may be determined in accordance with ASTM D 2504. The content of S-containing compounds in the bio-propane (such as H$_2$S or COS) calculated as elemental S may be determined in accordance with ASTM D 6667. The vapour pressure at 40° C. may be determined in accordance with EN ISO 8973. The density at 15° C. may be determined in accordance with EN ISO 8973.

35. The liquefied bio-propane composition according to any one of items 33 to 34, comprising at most 100 wt.-ppm, preferably at most 70 wt.-ppm, more preferably at most 50 wt.-ppm of H$_2$O.

The content of water may be determined in accordance with ASTM D 5454.

36. The liquefied bio-propane composition according to any one of items 33 to 35, comprising at most 5 mg/m$^3$, preferably at most 2 mg/m$^3$ of ammonia.

The content of ammonia may be determined with Drager tubes with the following principal: The drager detector pump has a pumping capacity of 100 cm$^3$. The materials being analyzed are drawn through a drager pump and reacts with chemicals inside the sample tubes to form a coloured compound. Equivalent concentration of the sample analyzed is read off from the scale where the coloured region ends. Equipment and Apparatus: Sample cylinder; Drager gas detector pump; Drager tubes Ammonia 2/a (2-30 ppm); Drager tubes Ammonia 5/a (5-70/50-600 ppm); Sample bags Tedlar® 2 liter (for gases); Sample bags Tedlar® 5 liter with metal fitting (for LPG).

37. The liquefied bio-propane composition according to any one of items 33 to 36, comprising at most 2000 wt.-ppm of methane, preferably at most 1500 wt.-ppm of methane, more preferably at most 1000 wt.-ppm of methane.

38. The liquefied bio-propane composition according to any one of items 33 to 37, comprising at most 2.0 wt.-% of ethane, preferably at most 1.5 wt.-% of ethane.

39. The liquefied bio-propane composition according to any one of items 33 to 38, comprising at most 10 wt.-ppm, preferably at most 5 wt.-ppm of S-containing compounds, calculated as elemental S.

41. The liquefied bio-propane composition according to any one of items 33 to 40 comprising at most 1000 wt.-ppm of unsaturated hydrocarbons, preferably at most 500 wt.-ppm, more preferably at most 250 wt.-ppm of unsaturated hydrocarbons.

42. The liquefied bio-propane composition according to any one of items 33 to 41, comprising at most 4.5 wt.-% of C3+ hydrocarbons.

43. The liquefied bio-propane composition according to any one of items 33 to 42, comprising at most 1.4 wt.-% hydrocarbons having 5 or more carbon atoms, preferably at most 1.0 wt.-%, more preferably at most 0.7 wt.-%, even more preferably at most 0.5 wt.-%.

The content of methane, ethane, propane, C3+ hydrocarbons, hydrocarbons having 5 or more carbon atoms, and/or of unsaturated hydrocarbons may be determined in accordance with ASTM D 2163.

44. The liquefied bio-propane composition according to any one of items 33 to 43, which is produced by the method according to any one of items 1 to 32.

45. A method for upgrading a bio-based material, comprising the steps of:
- (A) providing a bio-based fresh feed material of bio-renewable oils and/or fats having a glycerol-equivalent content of 2 wt.-% to 60 wt.-% relative to the total weight of the bio-based fresh feed material;
- (B) subjecting a hydrotreatment feed comprising the bio-based fresh feed material and an optional diluent to a hydrotreatment comprising HDO in the presence of a sulphided metal catalyst and hydrogen ($H_2$), to provide a hydrotreated effluent, wherein the hydrotreatment feed comprises 10-10 000 w-ppm of sulphur-containing compound calculated as elemental S;
- (C) subjecting the hydrotreated effluent to gas-liquid separation so as to provide a gaseous hydrotreated material comprising Hz, bio-propane, $H_2O$, $H_2S$, $CO_2$, and CO, and a liquid hydrotreated material comprising paraffinic hydrocarbons;
- (D) an optional step of subjecting the liquid hydrotreated material to fractionation, after an optional second hydrotreatment, and recovering at least diesel and/or kerosene range paraffinic hydrocarbon material;
- (E) subjecting the gaseous hydrotreated material to a purification step for removing $H_2S$ and $CO_2$ to obtain a $H_2S$ and $CO_2$ depleted gaseous stream;
- (F) subjecting the $H_2S$ and $CO_2$ depleted gaseous stream to $H_2$ recovering and drying to obtain dried $H_2S$, $CO_2$ and $H_2$ depleted gaseous stream;
- (G) fractionating the dried $H_2S$, $CO_2$ and $H_2$ depleted gaseous stream to recover a bio-propane gas composition, and optionally compressing the bio-propane gas composition to obtain a liquefied bio-propane composition;
- (H) subjecting at least part of the bio-propane gas composition and/or the liquefied bio-propane composition to a conversion comprising catalytic dehydrogenation to obtain a dehydrogenation effluent comprising bio-propylene;
- (I) recovering and optionally purifying a bio-propylene composition from the dehydrogenation effluent.

46. The method according to item 45, further comprising derivatisation of at least part of the bio-propylene composition to obtain at least one bio-monomer.

47. The method according to item 46, wherein the bio-monomer is at least one bio-monomer selected from the group consisting of bio-acrylic acid, bio-acrylonitrile, bio-acrolein and bio-propylene oxide.

48. The method according to item 46 or 47, wherein the derivatisation comprises at least one of oxidation and ammoxidation, wherein the oxidation is preferably carried out by gas phase oxidation.

49. The method according to any one of items 45 to 48, further comprising (co)polymerizing a mixture comprising at least part of the recovered bio-propylene composition and/or derivative(s) thereof and optionally co-monomer(s) and/or additive(s) to obtain a biopolymer composition.

The mixture may further comprise propylene and/or other (co)monomers and/or additives of fossil origin.

50. The method according to item 49, wherein the polymerisation is carried out in the presence of a polymerisation catalyst.

51. The method according to item 49 or 50, wherein the polymerisation is initiated by means of a polymerization initiator.

52. The method according to any one of items 45 to 51, comprising the step (D).

53. The method according to any one of items 49 to 52, wherein the polymer is further processed to produce a sanitary article.

54. The method according to any one of items 49 to 52, wherein the polymer is further processed to produce a construction material.

55. The method according to any one of items 49 to 52, wherein the polymer is further processed to produce a packaging material.

56. The method according to any one of items 49 to 52, wherein the polymer is further processed to produce a coating composition.

57. The method according to any one of items 49 to 52, wherein the polymer is further processed to produce a paint.

58. The method according to any one of items 49 to 52, wherein the polymer is further processed to produce a decorative material, such as a panel.

59. The method according to any one of items 49 to 52, wherein the polymer is further processed to produce an interior part of a vehicle, such as an interior part of a car.

60. The method according to any one of items 49 to 52, wherein the polymer is further processed to produce a rubber composition.

61. The method according to any one of items 49 to 52, wherein the polymer is further processed to produce a tire.

62. The method according to any one of items 49 to 52, wherein the polymer is further processed to produce a toner.

63. The method according to any one of items 49 to 52, wherein the polymer is further processed to produce a personal health care article.

64. The method according to any one of items 49 to 52, wherein the polymer is further processed to produce a part of a consumer good.

65. The method according to any one of items 49 to 52, wherein the polymer is further processed to produce a part or a housing of an electronic device.

66. The method according to any one of the preceding items, wherein the biopolymer composition comprises polypropylene (PP), ethylene-propylene-copolymer (EPM), or ethylene-propylene-diene-copolymer (EPDM).

67. The method according to item 66, further comprising a step forming a polymer product, such as a film, a molded product, a coating composition, a coating, a packaging, a construction material, a rubber composition, a tire, a part of a tire, or a gasket, from the polymer optionally together with other components.

68. The method according to any one of items 46 to 52, wherein the bio-monomer is at least one bio-monomer selected from the group consisting of bio-acrylic acid, an ester or a salt thereof.

69. The method according to item 68, comprising a step of polymerizing the bio-acrylic acid, an ester or a salt thereof, optionally in the presence of co-polymerizable monomer(s) and/or additive(s), to produce an acrylic polymer.

In this context, acrylic acid (and acrylic polymers) are meant to include any type of acrylic-based monomers and polymers, e.g. those based on (meth)acrylic acid, (meth) acrylic acid esters, (meth)acrylic acid salts, and (meth) acrylonitriles.

70. The method according to item 69, wherein the acrylic polymer is a water-absorbing polymer.

71. The method according to item 69 or 70, wherein the polymer is further processed to produce a sanitary article.

72. The method according to item 71, wherein the sanitary article is a diaper.

73. The method according to item 71, wherein sanitary article is a sanitary napkin.

74. The method according to item 71, wherein sanitary article is an incontinence draw sheet.

75. The method according to item 71, further comprising a step of mixing the acrylic polymer with further components to produce a coating or a paint.

76. The method according to any one of items 46 to 52, wherein the bio-monomer is propylene oxide.

77. The method according to item 76, comprising a step of polymerizing the propylene oxide, optionally in the presence of co-polymerizable monomer(s) and/or additive (s), to produce a polymer, such as a polyether, a polyether polyol, a polyester, a polyurethane, or a polymer or oligomer surfactant.

78. The method according to any one of items 46 to 52, wherein the bio-monomer is bio-butadiene and the derivatisation comprises a step of converting the bio-propylene material to produce bio-butadiene, optionally further comprising a step of purifying the bio-butadiene.

79. The method according to item 78, wherein the conversion step is a hydroreforming step.

80. The method according to item 78 or 79, comprising a step of polymerizing the bio-butadiene, optionally in the presence of co-polymerizable monomer(s) and/or additive (s), to produce a polymer, such as a polybutadiene rubber (BR), an acrylonitrile-butadiene rubber (NBR, HNBR), acrylonitrile-butadiene-styrene rubber (ABS), or styrene-butadiene rubber (SBR).

82. A biopolymer composition obtainable by the method according to any one of items 49 to 81.

BRIEF DESCRIPTION OF THE DRAWINGS

FIG. 1 is a flow chart illustrating an embodiment of the method of the present invention.

FIG. 2 is a flowchart illustrating embodiments of further processing the bio-propane composition in accordance with the present invention.

DETAILED DESCRIPTION OF THE INVENTION

In the following, the present invention is described in detail with reference to embodiments. The invention is not necessarily limited to the embodiments. Rather, the embodiments show preferable ways how the invention can be put into practice.

Terms and expressions used in the present invention are described below.

By the term "impurities" is meant those impurities harmful or undesired in the bio-propane composition and/or harmful during processing thereof. These impurities usually comprise metals, metal compounds, phosphorus, phosphorus compounds, nitrogen, nitrogen compounds, sulphur and compounds containing sulphur and oxygen containing compounds which are dissolved and/or miscible or chemically bound in the fresh feed oil or fat.

By the term "pre-treating bio-renewable oil(s) and/or fat(s)" is meant a conventional process or combinations of conventional processes aiming at purification of impure oil/fat feed, i.e. removal of impurities. Preferable pre-treatment comprises degumming, bleaching, heat treatment, centrifugation, filtering or any combination thereof which results in a decreased content of the impurities.

By the term "degumming" is meant a purification process wherein impure oil/fat is treated with acid, water and caustic at elevated temperature with high shear mixing. The formed gums may subsequently be separated from the oily material preferably by centrifugation and the material may be dried.

By the term "bleaching" is meant a purification process wherein acid and water is added to the impure oil/fat, and the resulting composition is mixed with an adsorbent material (such as bleaching earth) at elevated temperature and reduced pressure (such as vacuum). Thereafter the oil/fat is dried and separated from said adsorbent typically by filtration.

By the term "deodorization" is meant a purification process wherein oil is treated at an elevated temperature in reduced pressure and using steam stripping to remove impurities and/or free fatty acids.

By the term "hydrolysis of fat(s) and oil(s)" is meant a process where an oil(s) and/or fat(s) stream predominantly containing mono-, di- and triglycerides is hydrolysed to free up the fatty acids and glycerol using e.g. elevated temperature and water.

By the term "heat treatment" in the context of pre-treatment is meant a purification process wherein impure oil/fat is heated at elevated temperature to convert all or part of the soluble impurities into insoluble material that is subsequently removed for example by filtration or any other method.

By the term "hydrotreatment", sometimes also referred to as hydroprocessing, is meant a catalytic process of treating organic material by means of molecular hydrogen. Preferably, hydrotreatment removes oxygen from organic oxygen compounds as water i.e. hydrodeoxygenation (HDO), removes sulphur from organic sulphur compounds as dihydrogen sulphide ($H_2S$), i.e. hydrodesulphurisation, (HDS), removes nitrogen from organic nitrogen compounds as ammonia (NH3), i.e. hydrodenitrogenation (HDN), removes halogens, for example chlorine from organic chloride compounds as hydrochloric acid (HCl), i.e. hydrodechlorination (HDCl), removes metals by hydrodemetallization, and hydrogenates any unsaturated bonds present in the fresh feed. As used herein, by hydrotreatment is meant to cover also hydroisomerization.

By the term "hydrodeoxygenation" (HDO) is meant the removal of oxygen from organic molecules as water by means of molecular hydrogen under the influence of catalyst.

By the term "deoxygenation" is meant removal of oxygen from organic molecules, such as fatty acid derivatives, alcohols, ketones, aldehydes or ethers by any means previously described or by decarboxylation or decarbonylation.

In the present invention, the term "glycerol-equivalent content calculated relative to the total weight of the bio-based fresh feed material" means a content of glycerol and/or glycerol-based moieties in the bio-based fresh feed material and is calculated as if all glycerol (or glycerol-based) moieties (i.e. glycerol moieties in free glycerol and/or in monoglycerides, diglycerides or triglycerides, and/or glycerol-based moieties of e.g. partially deoxygenated glycerol, such as 1-propanol, 2-propanol, 1,2-propane diol or 1,3-propane diol and/or esters of these) were present as deprotonated glycerol (M=89.07 g/mol). In other words, the glycerol-equivalent content may be calculated as follows:

$$\text{glycerol-equivalent content}=(\text{Molar amount of glycerol-based moieties [mol]})*89.07 \text{ g/mol}/(\text{total mass of the bio-based fresh feed material [g]})$$

The term "bio-based" or "bio-renewable" indicates presence of a material derived from renewable sources. Carbon atoms of renewable or biological origin comprise a higher number of unstable radiocarbon ($^{14}$C) atoms compared to carbon atoms of fossil origin. Therefore, it is possible to distinguish between carbon compounds derived from renewable or biological sources or raw material and carbon compounds derived from fossil sources or raw material by analysing the ratio of $^{12}$C and $^{14}$C isotopes. Thus, a particular ratio of said isotopes can be used as a "tag" to identify renewable carbon compounds and differentiate them from non-renewable carbon compounds. The isotope ratio does not change in the course of chemical reactions. Examples of a suitable method for analysing the content of carbon from biological or renewable sources are DIN 51637, ASTM D6866 or EN 16640. As used herein, the content of carbon from biological or renewable sources is expressed as the biogenic carbon content meaning the amount of biogenic carbon in the material as a weight percent of the total carbon (TC) in the material, as determined in accordance with ASTM D6866. A biogenic carbon content of the total carbon content in a product, which is completely of biological origin, may be about 100 percent. The biogenic carbon content of the bio-based fresh feed material, hydrotreatment feed, diluent, bio-propane, bio-propylene and/or biopolymer according to the invention is lower in cases where other carbonaceous components besides biological components are used in the processing of the product but is preferably at least 5 percent.

In accordance with the invention, the term "bio-based" or "bio-renewable" or "bio-" in general means that at least a part of the material is a renewable material, i.e. has an amount of biogenic carbon content as a weight percent of the total carbon (TC) in the material, in accordance with ASTM D 6866. Preferably, the biogenic carbon content of the "bio-" material is at least 5 percent, more preferably at least 10 percent, at least 20 percent, at least 40 percent, at least 50 percent, at least 75 percent, at least 90 percent, or about 100 percent.

The biogenic carbon content of the bio-based fresh feed material is more preferably at least 50 percent, at least 75 percent, at least 90 percent, and particularly preferably about 100 percent.

The biogenic carbon content of the bio-propylene composition, the bio-monomer and/or the bio-polymer is preferably at least 0.1 percent, preferably at least 0.5 percent, at least 1 percent, at least 2 percent, at least 5 percent, at least 10 percent, at least 20 percent, at least 40 percent, more preferably at least 50 percent, at least 75 percent, at least 90 percent, or about 100 percent.

By the term "optionally" or "optional" is meant a characteristic, feature or step that may be present, but is not necessarily required for carrying out the invention.

All test method standards referred to in this text are the latest versions available at the filing date.

In the following, the method of the present invention will be described in greater detail with reference to preferred embodiments for the individual process steps and raw materials, intermediate products and end products. While the invention is not limited to the preferred embodiments, it is noted that any value or condition recited in the embodiments may be combined with the general process of the present invention either individually or in combination with other preferred embodiments.

Bio-Based Fresh Feed of Bio-Renewable Oil(s) and/or Fat (s)

The method of the present invention contains a step of providing a bio-based fresh feed material of bio-renewable oils and/or fats, i.e. a provision step (A).

Bio-renewable oil(s) and/or fat(s) (also referred to as bio-renewable feedstock) refer to a feedstock derived from a biological raw material component containing oil(s) and/or fat(s), usually containing free fatty acids and/or glycerides, such as plant oil/fats, vegetable oil/fats, animal oil/fats, fish oil/fats and algae oil/fats, or oil/fats from other microbial processes, for example genetically manipulated algae oil/fats, genetically manipulated oil/fats from other microbial processes and also genetically manipulated vegetable oil/fats. Components of such materials could also be used, such as for example alkyl esters (typically C1 C5-alkyl esters, such as methyl, ethyl, propyl, iso-propyl, butyl, sec-butyl esters). Bio-renewable (and "bio-based") oil(s) and/or fat(s) specifically excludes fossil oils.

In the present invention, it is possible to employ a bio-renewable feedstock (bio-renewable oil/fat) which is converted into a bio-based fresh feed material by a pre-treatment step. Alternatively, it is possible to employ an already pre-treated bio-based fresh feed material or it is possible to employ (crude, i.e. as-produced) bio-renewable oil(s) and/or fat(s) as a bio-based fresh feed material. In the present invention, reference is sometimes made to a bio-based fresh feed material (or feedstock), and this term shall encompass both a (non-pre-treated) bio-renewable feedstock and a pre-treated bio-renewable feedstock, unless stated otherwise.

The bio-renewable oils and/or fats further encompass a single kind of oil, a single kind of fat, mixtures of different oils, mixtures of different fats, mixtures of oil(s) and fat(s), fatty acids, glycerol and mixtures of the afore-mentioned.

These oils and/or fats typically comprise C10-C24 fatty acids and/or derivatives thereof, including esters of fatty acids, glycerides, i.e. glycerol esters of fatty acids, phospholipids, glycolipids, sphingolipids, etc. The glycerides may specifically include monoglycerides, diglycerides and triglycerides.

A typical bio-based fresh feed material is a glycidic raw material (or feedstock), which is a raw material (or feedstock) that contains glycerides, i.e. one, two or three fatty acids bound to glycerol through ester linkage. The bio-based fresh feed material (or feedstock) may also include (free) glycerol.

In the present invention, the bio-based fresh feed material of bio-renewable oils and/or fats comprises 2-60 wt.-% of glycerol-equivalent moieties (i.e. has a glycerol-equivalent content of 2-60 wt.-%). By selecting this kind of feedstock having a defined glycerol-equivalent content, or by adjusting the glycerol-equivalent content by adding free glycerol to a feedstock not meeting the defined content otherwise or by mixing feedstocks having different glycerol-equivalent contents, the bio-propane to impurities ratio in the gaseous hydrotreated material can be increased, while an excess temperature increase due to exothermic hydrotreatment reactions of the oxygen-rich glycerol moiety can be controlled.

Temperature control is important in the present invention because decarboxylation-reactions (as well as decarbonylation reactions) are generally favoured at higher hydrotreatment temperatures and such decarb reactions are undesired in the present invention, as will be explained later.

Glycidic raw materials (bio-renewable oil/fat) preferably include triglycerides of C10-C28 fatty acids, as well as mono- and di-glyceride variants thereof.

Examples of vegetable oils usable as a bio-based fresh feed material or as an origin thereof include, but are not limited to rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, *Brassica carinata* oil, and rice bran oil, or fractions or residues of above mentioned oils such as palm olein, palm stearin, palm fatty acid distillate (PFAD), purified tall oil, tall oil fatty acids, tall oil resin acids, tall oil unsaponifiables, tall oil pitch (TOP), and used cooking oil of vegetable origin.

Examples of animal fats usable as a bio-based fresh feed material or as an origin thereof include, but are not limited to tallow, lard, yellow grease, brown grease, fish fat, poultry fat, and used cooking oil of animal origin.

Further examples of usable oils and/or fats include microbial oils, including algal lipids, fungal lipids and bacterial lipids.

Pre-Treatment

The method of the present invention may comprise a pre-treatment step (A').

A typical problem with the use of bio-renewable oil(s) and/or fat(s), such as animal based fats or vegetable oils, in particular microbial oils, is that they tend to contain significant amounts of impurities such as metals, phosphorus, sulphur, nitrogen and oxygen. The impurities may cause problems, for example, in the hydrotreatment step or in the subsequent processing of the bio-propane composition, e.g. in form of catalyst poisons and/or coke precursors. Deposits of metals, phosphorus, sulphur, nitrogen and oxygen compounds are likely to result in catalyst deactivation and/or plugging of the reactor catalyst bed in refining processes.

Therefore, it can be beneficial to use a pre-treatment step (A') (pre-cleaning) for removal of these undesired components from the oil/fat product. Common treatment methods such as water degumming, soft degumming, acid degumming, wet bleaching, dry bleaching, evaporation and distillation, for example, are suitable to remove most of the impurities (contaminants) from a (crude) material of bio-renewable oil(s) and/or fat(s).

In the pre-treatment any conventional equipment may be used. For example pre-treatment comprising evaporation may involve use of one or more evaporators, such as one, or two or more consecutively arranged thin film evaporators, falling film evaporators, short path evaporators, plate molecular stills, or other evaporators using thin film evaporation.

The pre-treatment step may also (or exclusively) comprise a hydrolysis/transesterification step of glycerides and thus production of glycerol and fatty acids.

The pre-treatment step (A') can be particularly beneficial because unlike fossil material (mainly hydrocarbon material), the bio-renewable oil(s) and/or fat(s) almost exclusively consist of oxygenate material (such as glycerides), and the above-mentioned impurities can be removed from such oxygenate material much easier than from a fossil material, namely by simple pre-treatment step(s).

The method of the present invention thus can provide the benefit that a highly pure bio-propane composition can be produced with simple means. Further, such a highly pure bio-propane can be employed in a variety of subsequent upgrading processes, especially in processes tolerating only low amounts of impurities and/or catalyst poisons.

In the present invention, it is particularly preferable to employ a pre-treatment which reduces the amount of metal impurities because such metal impurities may promote decarb reactions in the hydrotreatment step, which is undesired in the present invention. The amount of alkali and alkaline earth metals in the fresh feed may be below 10 wt.-ppm, preferably below 5 wt.-ppm and more preferably below 1 wt.-ppm, calculated as elemental alkali and alkaline earth metals. The amount of other metals in the fresh feed may be below 10 wt.-ppm, preferably below 5 wt.-ppm, more preferably below 1 wt.-ppm, calculated as elemental metals.

Moreover, even a further upgraded material obtained from the bio-propane composition has low catalyst poisons (due to lower carry-over), thus allowing effective use thereof in a catalytic process, for example.

The pre-treatment may similarly comprise (or consist of) partial hydrogenation. In particular, the pre-treatment may comprise (partial or full) hydrogenation of double bonds contained in the bio-renewable oil(s) and/or fat(s). Such a procedure can further contribute to temperature control in the subsequent hydrotreatment step (B) because double bonds result in strongly exothermic reaction upon hydrotreatment.

Hydrotreatment

The method of the present invention comprises a hydrotreatment step (B) of subjecting a hydrotreatment feed comprising the bio-based fresh feed material, an optional diluent to a hydrotreatment comprising HDO in the presence of a sulphided metal catalyst and hydrogen ($H_2$), to provide a hydrotreated effluent.

The hydrotreatment feed (the feedstock subjected to hydrotreatment) may comprise at least 2 wt.-% of a bio-based fresh feed material (or feedstock), for example at least 3 wt.-%, at least 4 wt.-%, at least 5 wt.-%, at least 6 wt.-%, at least 7 wt.-%, at least 8 wt.-%, at least 9 wt.-%, at least 10 wt.-%, at least 11 wt.-%, at least 12 wt.-%, at least 15 wt.-%, at least 20 wt.-%, at least 25 wt.-%, at least 50 wt.-%, at least 75 wt.-%, at least 90 wt.-% or at least 95 wt.-%. The hydrotreatment feed may also be entirely of a bio-based fresh feed material or it may comprise 99 wt.-% or less of a bio-based fresh feed material, for example 90 wt.-% or less, 75 wt.-% or less, 50 wt.-% or less, 40 wt.-% or less, 35 wt.-% or less, 30 wt.-% or less, 25 wt.-% or less, 20 wt.-% or less, 15 wt.-% or less, or 10 wt.-% or less. Preferably, the summed amount of bio-based fresh feed material and diluent in the hydrotreatment feed is 95 wt.-% or more, more preferably 98 wt.-% or more, 99 wt.,-% or more, or 99.5 wt.-% or more. In addition to bio-based fresh feed material and diluent, an optional additional sulphur source for maintaining the activity of the sulphided metal catalyst may be employed. In the present invention, the hydrogen ($H_2$) which is employed in the hydrotreatment step (B) is not included when calculating the amount of bio-based fresh feed material and/or diluent in the hydrotreatment feed.

A hydrotreatment feed having lower amounts of bio-based fresh feed material may have advantages regarding temperature control. That is, the catalytic hydrotreatment of bio-based fresh feed material is exothermic, which means that blending the bio-based fresh feed material (or feedstock) with a diluent (e.g. a material that does not contain oxygen or a material that is not as prone to exothermic reactions during catalytic hydrotreatment conditions), preferably comprising paraffinic hydrocarbons, can avoid temperature increase or (local) overheating. Since high temperatures during hydrotreatment promotes decarb-reactions, the use of a diluent may help reducing the occurrence of such undesired reactions. On the other hand temperature control may be facilitated also by other means than diluting, e.g. by reactor design.

Blending or diluting may be done for example with diluent of mineral origin (fossil diluent), with a material of biological origin (e.g. a bio-renewable material other than the bio-based fresh feed material) or with a recycled paraffinic hydrocarbon product from e.g. catalytic hydrotreatment of the present process. Further, in case pre-treatment is carried out, blending/diluting may be done before pre-treatment, after pre-treatment or both before and after pre-treatment. Blending/diluting at least (preferably only) after pre-treatment and/or directly before the hydrotreatment step is favourable in view of process efficiency. If a recycled paraffinic hydrocarbon product from the catalytic hydrotreatment is used as a diluent, it can form at least 10 wt.-% of the hydrotreatment feed, or at least 25 wt.-%, at least 40 wt.-%, at least 50 wt.-%, at least 60 wt.-%, at least 70 wt.-%, at least 75 wt.-%, at least 80 wt.-%, at least 85 wt.-%, at least 90 wt.-%, or at least 92 wt.-%. The recycled paraffinic hydrocarbons can also form 98 wt.-% or less, such as 95 wt.-% or less, 92 wt.-% or less, 90 wt.-% or less, 85 wt.-% or less, 80 wt.-% or less, 70 wt.-% or less, 60 wt.-% or less, 40 wt.-% or less, or 25 wt.-% or less of the hydrotreatment feed. The same amounts may be employed in case the diluent is a fossil hydrocarbon material. Furthermore, the same amounts (summed amount) may be employed in case the diluent is a mixture of fossil hydrocarbons and recycled paraffinic hydrocarbon product. If a mixed diluent is employed (i.e. neither the fossil content nor the renewable content is 0), it is preferred that the fossil content (calculated as the content of fossil material having a biogenic carbon content of 0%) in the diluent be 90 wt.-% or less, preferably 80 wt.-% or less, 70 wt.-% or less, 60 wt.-% or less, 50 wt.-% or less, 40 wt.-% or less, 30 wt.-% or less, 20 wt.-% or less, 10 wt.-% or less.

Hydrotreatment, comprising e.g. hydrodeoxygenation of a bio-based fresh feed material to a hydrotreated effluent, may involve various reactions where molecular hydrogen reacts with other components, or components undergo molecular conversions in presence of molecular hydrogen and solid catalyst. The reactions include but are not limited to hydrogenation, hydrodeoxygenation, hydrodesulphurization, hydrodenitrogenation, hydrodemetallization, hydrocracking and hydroisomerization.

It is preferred that the hydrotreatment conditions are selected such that it provides saturated paraffinic hydrocarbons.

The hydrotreatment of the present invention is carried out in the presence of a sulphided metal catalyst and may comprise one or more of the following reactions:
1) hydrodeoxygenation (HDO), hydrogenation of oxygen bonds—removing oxygen as $H_2O$,
2) decarboxylation where oxygen is removed in the form of $CO_2$, and
3) decarbonylation where oxygen is removed in the form of CO.

Conventionally, the occurrence of decarb-reactions (decarboxylation and/or decarbonylation) in a hydrotreatment process has been regarded as being favourable because this oxygen removal route reduces the consumption of (expensive) hydrogen. However, the present inventors found that the carbon dioxide formed as a result of the abundant decarb-reactions may react with hydrogen sulphide (which is present in the hydrotreatment step in order to ensure the activity of the sulphided catalyst) during the hydrotreatment or the subsequent separation and/or purification steps, to produce carbonyl sulphide (COS). The presence of carbonyl sulphide is particularly problematic in the present invention because it has a boiling point which is similar to that of propane, and thus COS can hardly be separated from propane using conventional industry-scale techniques.

Preferably the hydrotreatment comprises HDO.

Many conditions for hydrotreatment/hydrodeoxygenation are known to the skilled person. The hydrotreatment of a bio-based fresh feed material in accordance with the present invention is carried out in the presence of a sulphided metal catalyst. The metal can be one or more Group VI metals, such as Mo or W, or one or more Group VIII non-noble metals such as Co or Ni. The catalyst may be supported on any convenient support, such as alumina, silica, zirconia, titania, amorphous carbon, molecular sieves or combinations thereof. Usually the metal will be impregnated or deposited on the support as metal oxides. They will then typically be converted into their sulphides. Examples of typical catalysts for hydrodeoxygenation are molybdenum containing catalysts, NiMo, CoMo, or NiW catalysts; supported on alumina or silica, but many other hydrodeoxygenation catalysts are known in the art and have been described together with or compared to NiMo and/or CoMo catalysts. The hydrodeoxygenation is preferably carried out under the influence of sulphided NiMo or sulphided NiW catalysts in the presence of hydrogen gas. Preferably, the hydrodeoxygenation is conducted in the presence of a sulphided metal catalyst, wherein the sulphided metal catalyst does not comprise CoMo.

The hydrotreatment may be performed under a hydrogen pressure from 1 to 200 bar, preferably from 10 to 100 bar, more preferably from 30 to 70 bar, at temperatures from 200 to 400° C., preferably from 230 to 370° C., and liquid hourly space velocities of 0.1 $h^{-1}$ to 3.0 $h^{-1}$, preferably of 0.2 to 2.0 $h^{-1}$.

By feeding the hydrogen ($H_2$) to hydrogenation so as to provide a ($H_2$ partial) pressure of 1-200 bar (preferably 10-100 bar, more preferably 30-70 bar), efficient HDO, HDN, and HDS reactions can be ensured while controlling decarb and/or cracking reactions at a low level.

During the hydrotreatment step (B) using a sulphided catalyst, the sulphided state of the catalyst is preferably maintained by addition of a sulphur-containing compound to the bio-based fresh feed material and/or to the diluent and/or fed along the hydrogen gas and/or separately to the hydrotreatment reactor. Usually, the sulphur is added in the form of $H_2S$, but it is nevertheless possible to add the sulphur in the form of other sulphur compounds such as sulphides, disulphides (e.g. dimethyl disulphide, DMDS), polysulphides, thiols, thiophene, benzothiophene, dibenzothiophene and derivatives thereof, as a single compound or a mixture of two or more types of these compounds. It is also possible to blend a sulphur containing mineral oil diluent with the bio-based fresh feed material.

According to the method of the present invention, the sulphur content of the hydrotreatment feed (the feed being subjected to hydrotreatment) is 10-10 000 wt.-ppm (ppm by weight), preferably 10-1000 wt.-ppm, more preferably 10-500 wt.-ppm, even more preferably 10-300 wt.-ppm, yet more preferably 10-200 wt.-ppm, and most preferably 20-100 wt.-ppm. By adjusting the sulphur content within this range, the occurrence of decarb-reactions may be controlled or suppressed, and the lower sulphur content in the feed is beneficial also for controlling or suppressing generation of COS as well. That is, while a minimum amount of sulphur ensures sufficient catalyst activity (and thus not necessitating high temperatures which would promote decarb-reactions), not exceeding the maximum amount can suppress the formation of (large amounts of) $H_2S$, which might convert into COS, so that no strong efforts need to be taken to get rid of this impurity after hydrotreatment. Furthermore, high sulphur contents tend to promote decarb-reactions during hydrotreatment.

Effective conditions for hydrodeoxygenation preferably reduce the oxygen content of the hydrotreatment feed to less than 1 wt.-%, such as less than 0.5 wt.-% or less than 0.2 wt.-%.

The hydrotreated effluent (crude material) is separated into a gas stream and a liquid stream to provide a gaseous hydrotreated material and a liquid hydrotreated material, respectively. The gaseous hydrotreated material comprises hydrogen that has not been used as well as propane and impurities, such as one or more of $H_2O$, $CO_2$, CO, COS, $H_2S$, $NH_3$, $PH_3$ and light hydrocarbons. As the bio-based fresh feed material contains glycerol-equivalent moieties, propane is obtained mainly from hydrogenation of the glycerol moieties, and to a much lesser extent, if any, from cracking of the fatty acids or the produced hydrocarbons.

Gas-Liquid Separation

The method of the present invention comprises a gas-liquid separation step (C).

After performing hydrodeoxygenation under effective conditions, as described above, propane will be present as one of a variety of gas phase components. In the gas-liquid separation step (C), the hydrotreated effluent is separated into a gaseous hydrotreated material and a liquid hydrotreated material. The gas-liquid separation step may be carried out as a separate step (after the effluent has left the hydrotreatment reactor or reaction zone) and/or as an integral step of the hydrotreatment step, e.g. within the hydrotreatment reactor or reaction zone. Majority of the water formed during HDO and potentially carried-over from the fresh feed may be removed for example via a water boot in the gas-liquid separation step, while typically traces entrain in the gaseous hydrotreated material.

The gaseous hydrotreated material comprises at least Hz, bio-propane, $H_2O$, $H_2S$, $CO_2$, and CO. That is, although the present invention preferably makes efforts to minimize the production of CO and $CO_2$, generation thereof can hardly be avoided in hydrotreatment of a bio-based fresh feed in accordance with the present invention.

Accordingly, the gaseous hydrotreated material includes hydrotreatment reaction products other than bio-propane, such as $H_2O$, $CO_2$ and CO from the hydrogenation and/or decarb-reactions, although the amounts of these side products will not necessarily represent the extent of these reaction types because of the water-gas shift reaction where CO and $H_2O$ are in equilibrium with $CO_2$ and $H_2$.

Additionally the gaseous hydrotreated material may include light hydrocarbons, for example as a result of cracking, in addition to the bio-propane. The light hydrocarbons include the gaseous light hydrocarbons, i.e. hydrocarbons that are in the gas phase at the pressure and temperature of the gas-liquid separation step. The light hydrocarbons may for example be hydrocarbons having fewer than seven carbon atoms, i.e. C1 to C6 hydrocarbons, which include, but are not limited to: methane, ethane, propane, butane, 2-methylpropane, pentane, isopentane, neopentane, hexane, 2-methylpentane, 3-methylpentane, 2,3-dimethylbutane, 2,2-dimethylbutane. In addition to light hydrocarbons, there could also be hydrocarbons having seven or more carbon atoms, for example C7 to C10 hydrocarbons, but they would normally only be present at most in a few tens of ppm.

Hydrogen is usually present in the gaseous hydrotreated material as a major component. The gaseous hydrotreated material may contain at least 70 mol-% hydrogen, such as at least 75 mol % hydrogen, at least 80 mol-% hydrogen. The hydrogen content may be less than 95 mol-%, such as less than 90 mol-%.

Bio-propane is also present in the gaseous hydrotreated material and the amount depends mainly on the content of glycerol-equivalent moieties in the raw material and to a lesser extent on cracking. Employing a bio-based fresh feed material of bio-renewable oils and/or fats having a glycerol-equivalent content of 2 wt.-% to 60 wt.-% relative to the total weight of the bio-based fresh feed material in the hydrotreatment feed ensures an industrially feasible amount of bio-propane in the gaseous hydrotreated material, although the content thereof may furthermore depend on the amount of diluent and/or the hydrogen to oil ratio [NI/I] (the ratio between the volume of hydrogen fed to the hydrotreatment step [NI] and the volume of the hydrotreatment feed [I]).

The present invention provides a flexible process allowing easy adjustment of the glycerol-equivalent content in the bio-based fresh feed, thereby obtaining diesel and/or kerosene and bio-propane in a ratio that best meets the prevailing or foreseen market demand.

In the present invention, the gaseous hydrotreated material preferably contains at least 1 mol-% bio-propane, such as at least 3 mol % bio-propane. The gaseous hydrotreated material may similarly contain 25 mol-% or less bio-propane, such as 20 mol-% or less, or 15 mol-% or less. When the gaseous hydrotreated material is derived from a bio-based fresh feed material of bio-renewable oils and/or fats having a glycerol-equivalent content of 2 wt.-% to 60 wt.-% relative to the total weight of the bio-based fresh feed material the content of the gaseous hydrotreated material is often 25 mol-% or less.

In various embodiments the temperature of the gaseous hydrotreated material is between 5° C. and 95° C., and the pressure is between 20 bar and 60 bar.

The liquid hydrotreated material obtained from the gas-liquid separation comprises at least paraffinic hydrocarbons. The majority of these paraffinic hydrocarbons will have a carbon number of more than 3 (C3+ hydrocarbons).

The gas-liquid separation step may be carried out at a temperature of 15° C. to 65° C., preferably of 20° C. to 60° C., and at the same pressure as that of the hydrotreatment step. In general, the pressure during the gas-liquid separation step may be 1-200 bar, preferably 10-100 bar, or 30-70 bar. The higher the pressure and/or the lower the temperature in the gas-liquid separation step, the higher the amount of condensed heavy components (e.g. C3+ hydrocarbons) in the liquid hydrotreated material, and thus less in the gaseous hydrotreated material.

Fractionation of the Liquid Hydrotreated Material

The step (D) comprises subjecting the liquid hydrotreated material to fractionation, after an optional second hydrotreatment, and recovering at least diesel and/or kerosene range paraffinic hydrocarbon material, in particular diesel range paraffinic hydrocarbon material meeting EN 590 requirements for automotive diesel fuel and/or kerosene range paraffinic hydrocarbon material meeting ASTM D7566-16b, Annex A2, meeting requirements for aviation turbine fuel.

The second hydrotreatment is an optional step and may be employed in accordance with need, e.g. in order to meet the oxygenate content requirements of the resulting fractions. Preferably, the second hydrotreatment comprises hydroisomerization so as to increase iso-paraffin content in the hydrocarbon material (liquid hydrotreated material), thereby improving cold properties of the diesel and/or kerosene range paraffinic hydrocarbon material.

The fractionation may be carried out using any conventional means.

The step (D) provides at least one of a kerosene range paraffinic hydrocarbon material and a diesel range paraffinic hydrocarbon material, in particular diesel range paraffinic hydrocarbon material meeting EN 590 requirements for automotive diesel fuel and/or kerosene range paraffinic hydrocarbon material meeting ASTM D7566-16b, Annex A2, meeting requirements for aviation turbine fuel.

The step (D) may also contain a water separation (sub) step. The water separation may be carried out after the second hydrotreatment or before the fractionation.

The step (D) is carried out after step (C) but needs not necessarily be carried out before step (E), (F), (G). Step (D) is preferably carried out concurrently with steps (E), (F), (G).

Purification of the Gaseous Hydrotreated Material

Depending on the composition of the gaseous hydrotreated material, it should undergo a purification step (E) before it is separated from hydrogen and dried.

The purification step (E) comprises at least subjecting the gaseous hydrotreated material to purification for removing $H_2S$ and $CO_2$ to obtain a $H_2S$ and $CO_2$ depleted gaseous stream. Preferably, the purification step (E) further comprises removing $NH_3$. $H_2S$, $CO_2$ or both $H_2S$ and $CO_2$ can be removed by sweetening the gaseous hydrotreated material to remove excess $H_2S$ and $CO_2$. The sour gas (containing $H_2S$ and/or $CO_2$) may be harmful to a membrane material optionally employed in a subsequent hydrogen recovery by membrane separation. Moreover, the presence of $H_2S$ in addition to $CO_2$ may result in formation of COS which cannot be easily separated from the bio-propane by distillation or fractionation. Since the formation of COS is an equilibrium reaction, it is shifted to the COS side by increasing the contents of $CO_2$ and $H_2S$ and by decreasing the content of $H_2O$. Thus, by removing $CO_2$ and $H_2S$ before drying, the formation of COS can be suppressed.

Sweetening of the gas should preferably reduce the $H_2S$ content to 1 wt.-ppm or lower, such as 0.5 wt.-ppm or lower, or 0.1 wt.-ppm or lower. Further, sweetening of the gas should preferably reduce the $CO_2$ content to 3000 wt.-ppm or lower, such as 2000 wt.-ppm or lower, or 1000 wt.-ppm or lower, or 500 wt.-ppm or lower, or 100 wt.-ppm or lower, or 10 wt.-ppm or lower, such as 1 wt.-ppm or lower, and $H_2S$ content to 50 wt.-ppm or lower, 10 wt.-ppm or lower, 5 wt.-ppm or lower, or such as 1 wt.-ppm or lower.

The gas may be sweetened using an amine scrubber, or another unit or processes used in e.g. refineries, at conditions that reduce or remove both the $H_2S$ and the $CO_2$.

The $H_2S$ which is removed from the gaseous hydrotreated material in step (E) may be recovered and recycled into the hydrotreatment step (B) as a sulphur source for maintaining the activity of the sulphided metal catalyst. In these embodiments such recycled $H_2S$ is calculated as being part of the specified range of sulphur-containing compound in the hydrotreatment feed (10-10 000 wt.-ppm, calculated as elemental S).

$H_2$ Recovery and Drying

The process of the present invention comprises a $H_2$ recovery and drying step (F) employing the $H_2S$ and $CO_2$ depleted gaseous stream provided in step (E).

In the method of the present invention, the drying may be carried out before $H_2$ recovery or the drying may be carried out after $H_2$ recovery. In view of processing efficiency, it is preferred that the drying is carried out after $H_2$ recovery. In this way smaller drying equipment is needed, requiring less space and lower investment cost.

In the present invention it is essential that at least the drying step is preceded by the purification step (E). Since drying step (or sub-step) removes water from the gaseous material, it is essential that $CO_2$ and $H_2S$ content has been reduced before drying so as to decrease risk of COS formation during drying.

In the present invention, separation of propane from hydrogen (i.e. hydrogen recovery) is preferably accomplished using a selective membrane (membrane separation) and this embodiment is described in detail below. However, the invention is not limited to this embodiment and other methods for separating propane from hydrogen (and optionally at the same time from other gaseous components) may be accomplished using any other suitable method, such as cryogenic distillation or swing adsorption.

Step a)

The method of recovering hydrogen (and at the same time providing a $H_2$ depleted gaseous stream) according to an embodiment of the invention involves a step of providing a membrane. The membrane has a feed side and a permeate side. The membrane works by being selective for hydrogen over propane, in that it preferentially permeates most of hydrogen and rejects most of propane. If present, the one or more of the further gases chosen from the group consisting of: CO and light hydrocarbons are also rejected together with propane, while $H_2O$, $CO_2$, $H_2S$ and $NH_3$ would be rejected or only partially rejected depending on the membrane type and conditions, e.g. temperature and pressure.

Step b)

The membrane separation involves passing a gas stream containing at least propane and hydrogen ($H_2$) across the feed side of the membrane that is hydrogen selective. A driving force for transmembrane permeation is provided by a higher pressure on the feed side than on the permeate side. For example, the pressure on the feed side can include a pressure of 10 barg or higher, such as 20 barg or higher, or 30 barg or higher, or 40 barg or higher, or 50 barg or higher and the pressure on the permeate side can include a pressure that is at least 1 bar lower than the feed side, such as 5 bar or lower, or 10 bar or lower, or 20 bar or lower, or 30 bar or lower. The membrane can be made from polymeric, ceramic or metal materials well known in the art of membrane science, such as cellulose acetate, polysulfone, polyimide, polyamide, zeolite, or palladium, and can be in form of spiral wound membrane, hollow fiber membrane, tube or plate.

Step c)

After the membrane separation stage, a retentate stream depleted in hydrogen and enriched in propane compared to the crude gas stream can be withdrawn from the feed side.

The retentate stream may contain less than 65 mol-% hydrogen, such as less than 55 mol %, less than 40 mol-%, less than 25 mol-%. The retentate stream may also contain more than 5 mol-% hydrogen, such as more than 10 mol-% hydrogen. The membrane is usually operated such that there will remain some hydrogen in the retentate stream because it will result in a higher purity of hydrogen in the permeate stream. This very pure hydrogen may be recycled to any of the hydrotreatment steps in the present process.

The retentate stream may also contain more than 15 mol-% propane, for example more than 25 mol-% propane, more than 30 mol-% propane. The retentate stream may also contain less than 75 mol-% propane, such as less than 65 mol-% propane, or less than 55 mol-% propane.

Step d)

After membrane separation stage, a permeate stream enriched in hydrogen and depleted in propane compared to the crude gas stream can be withdrawn from the permeate side.

In this embodiment employing membrane separation, it is preferred that the membrane stage cut, defined as the fraction of the gas stream that permeates the membrane, may correspond to at least 10%, such as at least 15%, or at least 20%, at least 25%, at least 30%, at least 40%, at least 50%, or at least 75%. The stage cut can also correspond to 95% or less, such as 80% or less, 70% or less, 50% or less. The higher the stage cut, the less pure the hydrogen in the permeate will be. The permeate stream may be used as a recycle hydrogen gas.

As said before, the step (F) further comprises a drying stage (sub-step). Drying may be accomplished using any conventionally known chemical and/or physical method, e.g. using an adsorbent and/or absorbent for water. One particularly preferred embodiment involves drying using molecular sieve dehydration beds.

Fractionation and Optional Compressing

The dried $H_2S$, $CO_2$ and $H_2$ depleted gaseous stream obtained in step (G) is forwarded to a fractionation step (F) to recover a bio-propane gas composition.

Within step (F) and during or after the fractionation, the bio-propane gas composition (or a precursor thereof) may be compressed in order to provide a liquid bio-propane composition.

The dried $H_2S$, $CO_2$ and $H_2$ depleted gaseous stream is depleted in hydrogen and enriched in propane compared to the gas stream entering the membrane separation stage and is subjected to fractionation by distillation, such as cryogenic separation and/or elevated pressure distillation in order to separate at least hydrogen from propane.

An elevated pressure distillation may be conducted in a pressurised distillation column, where there is a vertical temperature gradient. In various embodiments the elevated pressure distillation could be considered cryogenic separation, in that the elevated pressure distillation may be conducted at temperatures above −100° C., such as above −85° C., above −70° C., such as above 0° C. The temperature range for the distillation column is preferably from −70° C. to 130° C. The bottom of the pressurised distillation column (measured at the valve from which of the column's bottom product is withdrawn) may have a temperature of 80° C. to 130° C.

The elevated pressure distillation is preferably conducted so as to ensure sufficient theoretical plates so that hydrogen and other light hydrocarbons such as C1 (methane) and C2 (ethane and ethylene) as well as residual CO, $CO_2$ can be separated from bio-propane. In the lower section of the column, the bio-propane is separated from residual C4, C5 and higher hydrocarbons. These may be purged with a small portion of the bio-propane, back to the diesel stabilisation section of a renewable diesel plant. If further gas species are present, which include, but are not limited to CO and $CO_2$ and other gaseous light hydrocarbons in addition to propane, it is advantageous that conditions are provided to ensure sufficient theoretical plates to separate propane from the further gas species such that the resulting propane composition has a bio-propane content of preferably at least 90 wt.-%.

The elevated pressure distillation may be conducted at pressures above 20 bar (gauge), such as between 25 and 40 bar (gauge). The elevated pressure distillation may be performed between −70° C. and 130° C. at such pressures. For example between 0° C. and 130° C.

The bio-propane composition obtained from the elevated pressure distillation may be formulated into a propane-containing product. More specifically, the bio-propane gas composition may be compressed to give a liquid bio-propane composition. The compressing may be conducted after the fractionation to give the liquefied bio-propane composition or may be conducted in the course of an elevated pressure fractionation/distillation, e.g. in case the propane is in liquid state under the conditions employed in the fractionation at least at the stage where propane is withdrawn from the fractionation stage.

In other words, the present invention provides a bio-propane gas composition and/or a liquid bio-propane composition (which may commonly be designated as bio-propane composition).

In the present invention, the bio-propane composition obtained from the elevated pressure distillation and optional compression stage preferably has a minimum propane content of 90 wt.-% and/or a maximum propylene content of at most 1500 wt.-ppm, with or without further formulation. The remainder of the composition will usually be light hydrocarbons, such as iso-butane, butane, ethane, methane. For example the propane obtained may—with or without further formulation—fulfil one or more of EN 589, DIN 51622, BS 4250 or HD 5 propane specifications.

Preferably, the bio-propane composition obtained from the elevated pressure distillation (and optional compression stage) contains only little or no propylene. This may be contributed by the fact that the bio-propane is derived from a source that does not contain propylene to start out with, e.g. if conditions for hydrotreatment has been sufficiently severe to ensure that all existing olefins have been hydrogenated and no olefins are formed. Keeping the olefins content (such as the propylene content) of the bio-propane composition low (or not containing olefins) reduces the coking tendency in subsequent catalytic upgrading processes.

Preferably the liquefied bio-propane composition comprises at most 1500 wt.-ppm, preferably at most 1000 wt.-ppm, more preferably at most 800 wt.-ppm, even more preferably at most 500 wt.-ppm of propylene.

According to the present invention, the propane product is dehydrogenated to propylene.

The hydrogen obtained in the fractionation stage may be at least partly recycled to the hydroprocessing step (B), optionally together with the permeate stream of the membrane separation stage. Alternatively, or in addition, part of the hydrogen obtained from the elevated pressure distillation may be recycled into other processes requiring hydrogen.

Membrane

The membrane employed in the preferred membrane separation process is hydrogen selective, in that it selectively permeates hydrogen. Various hydrogen permeable membranes are known in the art, and some of the membranes are based on polymeric, ceramic or metal materials well known in the art of membrane science, such as polysulfone, polyimide, polyamide, cellulose acetate, zeolite or palladium. The membrane may have any suitable shapes and sizes, such as for example it may be in the form of a spiral wound membrane, hollow fibre membrane, tube membrane or plate membrane. The actual selectivity for hydrogen over propane depends on the material that the membrane is made out of, as well as the process conditions, including the temperature and the pressure on the feed side and the permeate side, respectively.

The membrane material and conditions for membrane separation is preferably chosen so that the membrane being selective for hydrogen over propane exhibits a selectivity for hydrogen over propane of at least 5, such as at least 10, at least 20, at least 30, at least 50, or at least 60, measured as pure component permeability ratio (vol/vol).

In some embodiments a membrane is provided having a feed side and a permeate side, the membrane being selective for hydrogen over propane. A crude gas stream comprising between 75 and 90 mol % hydrogen and between 5 and 10 mol % propane is being passed across the feed side of the membrane resulting in a retentate gas stream and a permeate gas stream. The retentate gas stream being depleted in hydrogen (between 40 and 60 mol %) and enriched in propane (between 30 and 50 mol %). The permeate gas stream being hydrogen enriched (more than 96 mol %) and depleted in propane (less than 0.5 mol %). Subjecting then the retentate stream to elevated pressure distillation to further separate hydrogen from pressure yields a combined hydrogen recovery of more than 85 mol %.

Dehydrogenation of Propane

The bio-propane composition of the present invention may be subjected to a dehydrogenation step to prepare a propylene composition.

Since the bio-propane composition of the present invention has low impurity levels and in particular contains only low amounts of dehydrogenation catalyst poisoning impurities, and coke precursors and coke-promoting impurities, the bio-propane composition is exceptionally well suited for dehydrogenation.

That is, the inventors of the present invention found that the common understanding (which was derived from fossil-based treatments) that coke is mainly caused by heavy (C3+) and sulphur-containing impurities is incomplete and cannot be directly related to bio-based propylene materials.

More specifically, the present inventors surprisingly found that CO and $CO_2$, which usually occur in hydrotreated bio-material in significant amounts, may cause coking as well. Although it is not desired to be bound to theory, it is assumed that the coking tendency of these impurities is caused by e.g. disproportionation of CO to $CO_2$ and C, while the $CO_2$ may generate CO under the conditions of the further processing stage, e.g. dehydrogenation.

In addition, while the removal of sulphur-containing impurities was known already for fossil propane to be subjected to dehydrogenation, the present inventors found that the presence of CO and $CO_2$ in addition to sulphur-containing compounds may generate COS. This impurity cannot be easily separated from the bio-propane composition and thus remains in the composition. That is, as said above, using common fractionation techniques, usually more than 90 wt.-% of the COS of the original material is carried over the bio-propane composition in a common fractionation stage. Therefore, the present invention takes measures to avoid the production of COS and to promote removal of COS in the hydrotreatment and purification process preceding the fractionation stage.

Similarly, the present invention takes measures to remove metal-containing, including metalloid-containing (specifically Si-containing) impurities, since these impurities are considered to promote coking tendency as well.

Thus, a highly suitable feed for a catalytic dehydrogenation process and other catalytic processes can be provided.

In the dehydrogenation process, bio-propane composition is contacted with a catalyst. The contacting may be accomplished in a fixed catalyst bed system, a moving catalyst bed system, a fluidized bed system, or a in a batch-type operation, e.g. in a stirred reactor. The dehydrogenation reactor may comprise one or more separate reactor zones with heating. The bio-propane gas composition may be contacted with a catalyst (e.g. a catalyst composite) in either upward, downward or radial flow fashion. The propane may be in the liquid phase, a mixed vapor-liquid phase or the vapor phase when contacting the catalyst. Preferably, the propane is in the vapor phase.

Dehydrogenation conditions preferably include a temperature of from 150° C. to 820° C., a pressure of from 0.1 to 2530 kPa (absolute) and a liquid hourly space velocity of about 0.01 to about 50 $h^{-1}$.

The dehydrogenation is more preferably carried out at a temperature of from 540° C. to 650° C., even more preferably from 560° C. to 630° C.

In addition, the dehydrogenation is more preferably carried out at a pressure of from 0.4 to 500 kPa (absolute), even more preferably from 0.5 to 400 kPa.

In addition, the dehydrogenation is more preferably carried out at a liquid hourly space velocity of about 1 to about 30 $h^{-1}$, even more preferably about 5 to about 25 $h^{-1}$.

Accordingly, the most preferred conditions are a temperature of from 560° C. to 630° C., a pressure of from 0.5 to 400 kPa and a liquid hourly space velocity of about 5 to about 25 $h^{-1}$.

The dehydrogenation catalyst (or catalyst composite) should exhibit high activity, high selectivity and good stability. Preferred catalytic composites comprise group VIII noble metal(s) (preferably Pt and/or Pd) and a solid inorganic carrier. Such catalytic composites are well known to those skilled in the art. Other preferred catalytic composites comprise a group VIII noble metals (preferably Cr) and a solid inorganic carrier. Particularly preferred catalyst composites include the platinum on alumina catalysts and chrome on alumina catalysts. For example, the dehydrogenation catalysts disclosed in US 2015/259265 A1 and US 2003/191351 A1, both documents being incorporated by reference, can be preferably used.

After the dehydrogenation is completed, at least a bio-propylene composition is recovered from the dehydrogenation effluent. Recovering the bio-propylene composition can be achieved using any commonly known means, such as drying and/or fractionation.

Bio-Propylene Composition

The term "bio-propylene composition" refers to the product recovered from the dehydrogenation effluent while the term "dehydrogenation effluent" refer to products obtained directly after a dehydrogenation step. As used herein, the term "dehydrogenation product" may also refer to the mixture of hydrocarbons obtained directly after the dehydrogenation step as such.

Since the bio-propane composition of the present invention is very pure, the bio-propylene composition (and actually already the dehydrogenation effluent) is very pure as well and virtually no harmful impurities are carried over to the bio-propylene composition. Thus, the bio-propylene composition is particularly suitable for subsequent catalytic processes, such as catalytic polymerisation, catalytic (partial) oxidation, catalytic C—C-coupling reactions and the like.

Upgrading or Using Bio-Propylene Composition

The bio-propylene composition obtained or obtainable with the embodiment of the invention is particularly suitable as raw materials for conventional petrochemistry, and polymer industry. Thus, the propylene can be added to the known value-added chain while no significant modifications of production processes are required.

For example, the bio-propylene composition may be further modified to give derivatives of propylene. Propylene derivatives, which may be produced in accordance with the present invention, include, among others, isopropanol, acrylonitrile, propylene oxide, acrylic acid, allyl chloride, oxoalcohols, cumens, acetone, acrolein, hydroquinone, isopropylphenols, 4-hethylpentene-1, alkylates, butyraldehyde, ethylene-propylene elastomers, and their derivatives. Propylene oxide derivatives include, for example, propylene carbonates, allyl alcohols, isopropanolamines, propylene glycols, glycol ethers, polyether polyols, polyoxypropyleneamines, 1,4-butanediol, and their derivatives. Allyl chloride derivatives include, for example, epichlorohydrin and epoxy resins. Isopropanol derivatives include, for example, acetone, isopropyl acetate, isophorone, methyl methacrylate, and their derivatives. Butyraldehyde derivatives include, for example, acrylic acid, acrylic acid esters, isobutanol, isobutylacetate, n-butanol, n-butylacetate, ethylhexanol, and their derivatives. Acrylic acid derivatives include, for example, acrylate esters, and their derivatives.

The bio-propylene composition or the propylene derivative(s) may further be subjected to additional processes, such as polymerization, to provide subsequent products, such as polymers. Examples of such polymers include polypropylene, polymethyl methacrylate, polyacrylates and water-absorbing polymers such as superabsorbents.

The bio-propylene composition of the present invention may be used in a wide variety of applications and/or for preparing materials to be used in these applications. Such applications are, for example, consumer electronics, composites, automotive, packaging, medical equipment, agrochemicals, coolants, footwear, paper, coatings, adhesives, inks, pharmaceuticals, electric and electronic appliances, sport equipment, disposables, paints, textiles, super absorbents, building and construction, fuels, detergents, furniture, sportwear, solvents, plasticizers, high octane gasoline, synthetic rubber and perfumes.

The bio-propylene composition and/or bio-propylene derivative(s) obtained therefrom may further be subjected to polymerization to provide polymers (bio-polymers). In the following, reference will be made to "propene" and "propene derivatives" and this shall be understood to cover the bio-propylene composition, purified (isolated) bio-propylene obtained from the bio-propylene composition as well as bio-propylene derivatives in as-prepared, purified and/or isolated quality.

Purification and Polymerisation

The method of the present invention may further comprise subjecting at least a portion of the propylene rich dehydrogenated product (bio-propylene composition) to a purification treatment to remove at least one of CO, $CO_2$, or dienes/alkynes. An advantage of the method of the present invention is a low total amount of CO, $CO_2$, and dienes/alkynes and consequently a reduced burden of removal of CO, $CO_2$, dienes/alkynes, or a combination thereof, from the propylene rich dehydrogenated product. This is particularly advantageous in embodiments were at least a portion of the propylene rich dehydrogenated product is subjected to a polymerisation treatment.

As mentioned previously, CO, $CO_2$, and dienes/alkynes are polymerisation catalyst poisons and thus undesirable in a polymerisation process. The burden of removal of CO, $CO_2$, dienes/alkynes, or a combination thereof, from a portion of the dehydrogenation product (bio-propylene composition) to be subjected to a polymerisation treatment may be greatly reduced, potentially even redundant.

In practice, however, a portion of the dehydrogenation product to be subjected to a polymerisation treatment is usually first subjected to a purification treatment, for example, as a precaution or to avoid deviations from standard procedures. In any case, a lower amount of CO, $CO_2$, and/or dienes/alkynes impurities in the dehydrogenation product increases the life time of active material, such as an absorbent, an adsorbent, a reactant, a molecular sieve and/or a purification catalyst, which may be used in the purification treatment to remove at least one of CO, $CO_2$, or dienes/alkynes, and decreases the regeneration frequency of the active material.

The purification treatment to which at least a portion of the dehydrogenation product may be subjected can be any purification treatment suitable for removing at least one of CO, $CO_2$, or dienes/alkynes. Examples of such purification treatments are described in EP2679656A1, WO2016023973, WO2003048087, and US2010331502A1, all of which are incorporated herein by reference in their entirety.

The purification treatment may comprise contacting at least a portion of the dehydrogenation product with an active material, such as an absorbent, an adsorbent, a purification catalyst, a reactant, a molecular sieve, or a combination thereof, to remove at least one of CO, $CO_2$, or dienes/alkynes. Optionally, the purification treatment may comprise contacting at least a portion of the dehydrogenation product with the active material in the presence of molecular oxygen, molecular hydrogen, or both. In certain embodiments, the purification treatment comprises passing at least a portion of the dehydrogenation product through at least one purification train comprising active material, or at least one bed of active material. The contacting may be performed in a single vessel. Optionally, the contacting may be performed in multiple vessels preferably connected in series, i.e. allowing the portion of the dehydrogenation product to be purified to be passed from one vessel to the next for further purification.

The active material may comprise, for example, copper oxide or a copper oxide catalyst, oxides of Pt, Pd, Ag, V, Cr, Mn, Fe, Co, or Ni optionally supported on alumina, $Au/CeO_2$ optionally supported on alumina, zeolites, in particular type A and/or type X zeolites, alumina based absorbents or catalysts, such as a Selexsorb™ COS or Selexord™ CD, a molecular sieve comprising alumina, aluminosilicates, aluminophosphates or mixtures thereof, or any combination thereof. The active material may comprise an adsorbent or adsorbents as described in WO03/048087A1 on p. 11, ||12-p. 12, ||. 3; p. 12, ||. 18-p. 15, ||. 29, and/or p. 17, ||. 21-p. 21, ||. 2 and/or a molecular sieve or molecular sieves as described in WO03/048087A1 on p. 21, ||. 3-p. 22 ||. 26. The active material may comprise a purification catalyst or catalysts as described in US2010/0331502A1, paragraphs [0105] to [0116], or a molecular sieve or molecular sieves as described in US2010/0331502A1, paragraphs [0117] to [0119]. The active material may comprise a purification catalyst or catalysts as described in WO2016/023973A1, paragraph [0061], [0062], [0063], and/or [0064].

The purification treatment may be a purification treatment as described in EP2679656A1, paragraphs [0043] to [0082]. The purification treatment may be a purification treatment as described in US2010/0331502A1, paragraphs [0092] to [0119], and/or paragraph [0126], and/or Example 2. The purification treatment may be a purification treatment as described in WO2016/023973A1, paragraphs [0056] to [0067]. The purification treatment may be a purification treatment as described in WO03/048087A1, p. 11, ||. 12-p. 15, ||. 29, and/or p. 16, ||. 1-p. 21, ||. 2, and/or p. 23, ||. 14-p. 24, ||. 13, and/or Example 1 and/or Example 2.

Typically, impurities deactivate or foul the active material during purification treatment. Thus, the active material may be regenerated to at least partially regain its purification activity. Any regeneration process suitable for re-activating the active material may be used. For example, the active material may be regenerated as described in WO2016/023973A1, paragraphs p. 12, ||. 3-10, or as described in EP2679656A1, paragraphs [0108] to [0118], or as described in WO03/048087A1, p. 24, ||. 14-p. 25 ||. 32. For example, a CuO catalyst may be regenerated by contacting the CuO catalyst with $H_2$. A $CuO_2$ catalyst may be regenerated by contacting the $CuO_2$ catalyst with molecular oxygen. A zeolitic molecular sieve may be regenerated by applying heat and contacting the zeolitic molecular sieve with an inert gas flow, such as a nitrogen flow.

The purification treatment may comprise at least one of the following steps: i) contacting at least a portion of the dehydrogenation product with a CuO catalyst to remove oxygen, ii) contacting at least a portion of the dehydrogenation product with $H_2$ to remove dienes/alkynes by hydrogenation, iii) contacting at least a portion of the dehydrogenation product with a $CuO_2$ catalyst to remove CO by oxidation, or iv) contacting at least a portion of the dehydrogenation product with a zeolitic molecular sieve to remove $CO_2$. Optionally, the purification treatment may comprises removing secondary impurities, such as at least one of COS, $H_2S$, or $CS_2$, by contacting at least a portion of the dehydrogenation product with anactivated alumina catalyst, such as Selexorb™.

The method of the present invention may comprise subjecting at least a portion of the dehydrogenation product to a polymerisation treatment to form polymers. The portion of the dehydrogenation product subjected to the polymerisation treatment may be obtained directly from the dehydrogenation process or from the purification treatment described in the previous sections. Optionally, the portion of the dehydrogenation product subjected to the polymerisation treatment may partially have been subjected to the purification treatment described in the previous sections and partially be obtained directly from the dehydrogenation process.

As mentioned previously, due to the low amount of CO, $CO_2$, and dienes/alkynes in the dehydrogenation product formed in the manufacture or dehydrogenation step, subjecting the dehydrogenation product or a portion thereof to a purification treatment before polymerisation may be redundant. Consequently, the method of the present invention may comprise subjecting the propylene fraction (i.e. the bio-propylene composition) of the dehydrogenation product to a polymerisation treatment to form polypropylene without further purification.

The polymerisation treatment may include solution polymerisation, gas-phase fluidized bed polymerisation, slurry phase polymerisation, such as bulk polymerisation, high-pressure polymerisation, or a combination thereof. The polymerisation treatment may be performed in one or more polymerisation reactors. Each of the one or more polymerisation reactors may comprise multiple polymerisation zones. The composition of the feed fed to the polymerisation zones may vary between the zones.

For example, different portions of the dehydrogenation product may be fed to different zones and a comonomer may optionally be fed to one or more of the polymerisation zones. The comonomer fed to the polymerisation zones may be a different comonomer for different polymerisation zones. The polymerisation reactor may, for example, be a continuous stirred tank type reactor, a fluidised bed type reactor, such as a gas-phase fluidised bed reactor, or a stirred gas-phase type reactor in horizontal or vertical configuration.

Preferably, the polymerisation treatment is catalytic polymerisation. The polymerisation treatment may specifically comprise contacting at least a portion of the dehydrogenation product with a polymerisation catalyst optionally in the presence of molecular hydrogen to form polymers. Preferably, the contacting is performed in one or more polymerisation reactors.

In embodiments, wherein the polymerisation treatment is a catalytic polymerisation treatment, the molecular weight of the formed polymers may be regulated, for example, by the presence of hydrogen in the polymerisation treatment or by controlling the reaction temperature, depending on the polymerisation catalyst(s) employed. In embodiments, wherein the polymerisation treatment is a catalytic polymerisation treatment, the polydispersity is preferably mainly controlled by the catalyst employed. The polymerisation treatment may be a polymerisation treatment forming polymers having monomodal, bimodal, or multimodal molecular weight distributions. Bimodality or multimodality may be achieved by employing a bi-functional catalyst system in one reaction media (i.e. one reactor or polymerisation zone), or with a typical catalyst (i.e non-bi-functional) but with variable reaction media (i.e. combination of multiple polymerisation zones or multiple polymerisation reactors with different feeds). Other properties of the polymers formed in the polymerisation treatment, such as polarity, unsaturation content and/or polydispersity, may be controlled by controlling the reaction temperature, pressure and residence time, or through injecting a predetermined type and amount of co- and/or termonomers to the polymerisation process at a predetermined location, e.g. in one or more of the polymerisation zones optionally comprised in the polymerisation reactor(s).

Optionally, the density, elastic modulus and other properties of the polymers formed in the polymerisation treatment may be controlled by introducing to the polymerisation treatment a comonomer or combinations of multiple monomers, for example at least one of ethylene (in polypropylene production), propylene (in polyethylene production), 1-butene, 1-hexene (also (1,5-hexadiene), 1-octane (also 1,7-octadiene) and 1-decene (also 1,9-octadiene) or higher alpha olefins or alpha-omega dienes.

In certain embodiments, the polymerisation treatment may be a slurry polymerisation treatment comprising dissolving in a diluent, such as propane, propene or hexane, at least a portion of the dehydrogenation product together with molecular hydrogen, and optionally a comonomer, to form a solution, and contacting the solution with a catalyst to form polymers.

The polymerisation treatment may be a polymerisation treatment as described in EP2679656A1, paragraphs [0090]-[0097]. The polymerisation treatment may be a polymerisation treatment as described in US2010/0331502A1, paragraphs [0050]-[0066], and/or paragraphs [0123]-[0125], and/or Example 3. The polymerisation treatment may be a polymerisation treatment as described in WO2016/023973, paragraphs [0006]-[0020], and/or paragraphs [0024]-[0043]. The method may comprise a combination of a purification treatment and a polymerisation treatment as described in US2010/0331502A1, paragraphs [0092]-[0119]. Polypropylene (PP), or co- or terpolymers thereof, is thus formed in the polymerisation treatment. Polypropylenes of different density ranges and product classes, such as homopolymers, high crystallinity homo-polymers, random co-polymers, impact co-polymers, block co/terpolymers, hetero-phasic co-polymers, or combinations thereof may be formed in the polymerisation treatment of the propylene fraction. Similarly, the process conditions and catalysts mentioned in WO9924478 A1, WO9924479 A1, or WO0068315A1 may be used in the present invention.

An example of a polymerisation catalyst for catalytic polymerisation is Ziegler type catalysts, which utilise aluminum alkyl compounds, such as trimethylaluminum, triethylaluminum, tri-isobutylaluminum, methylaluminoxane (MAO), or tri-n-hexylaluminum as co-catalyst activators to activate titanium or vanadium sites on the catalyst, such as titanium tetrachloride. The aluminium alkyl compounds can additionally be used as scavengers of polymerisation poisons in the reaction media.

Preferable polymerisation catalysts which may be employed in accordance with the invention are furthermore those mentioned in EP0591224, EP1028985, which are herewith incorporated by reference in their entirety.

The polymerisation catalyst for catalytic polymerisation may be supported if desired or required by the process. The support material may be magnesium dichloride or silica support onto which active sites and optionally internal donors, such as benzoate, phthalate, diether, or succinate may be impregnated. Additionally, external donors, such as ethyl p-ethoxybenzoate (PEEB), dicyclopentyldimethoxysilane (DCPMS), diisopropyldimethoxysilane (DIPS), diisobutyldimethoxysilane, cyclohexyldimethoxymethylsilane (CHMMS), dicyclopentyldimethoxysilane (DPDMS), or alkoxysilanes, such as $Me(EtO)_3Si$, $Ph(EtO)_3Si$, $Ph_2(MeO)_2Si$, $Ph_2(EtO)_2Si$, $Ph(EtO)_3Si$, may be added to the polymerisation treatment.

In certain embodiments, the polymerisation catalyst may be stereo modifiers, such as cyclohexylmethyldimethoxysilane, dicyclopentyldimethoxysilane, diisobutyldimethoxysilane, diisopropyldimethoxysilane, isobutylisopropyldimethoxysilane, n-propyltrimethoxysilane, isobutylmethyldimethoxysilane, tetraethoxysilane, tetramethoxysilane, isobutyltriethoxysilane, n-propyltriethoxysilane, isobutyltrimethoxysilane, and/or cyclohexylethyldimethoxysilane.

A further example of a polymerisation catalyst for catalytic polymerisation are so called single site catalyst systems of which there are various types, such as Kaminsky type, combination type, constrained-geometry type, and late transition metal catalyst type.

The polymerisation catalyst may contain a metallocene complex of zirconium, titanium, or hafnium which usually contains two cyclopentadienyl rings or monolobal equivalents to cyclopentadienyl and either a perfluorinated boron-aromatic compound, an organoaluminum compound, or methylaluminoxane where the rings contain various alkyl substituents, both linear and cyclic. Said rings may be linked together by bridging groups. Alternatively, the polymerisation catalyst may contain monocyclopentadienyl derivatives of titanium or zirconium, one of the carbon atoms in the cyclopentadienyl ring being additionally linked to the metal atom by a bridge. These complexes which may be contained in the polymerisation catalyst are typically converted to polymerization catalysts by reacting said complexes with methylaluminoxane or by forming ionic complexes with noncoordinative anions. Other complexes, such as cyclopentadienyl group 4 ketimide complexes, cyclopentadienyl group 4 siloxyl complexes, and/or non-cyclopentadienyl group 4 phosphinimide complexes may optionally be used for forming polymerisation catalysts.

A further type of polymerisation catalysts for catalytic polymerisation is Phillips type catalysts which may comprise hexavalent chromium supported on a high-surface-area, wide-pore oxide carrier, such as silica, alumina, titania, aluminophosphates, or combinations where a mixture of chromium oxide and silicon oxide ($CrO_3/SiO_2$) may be used to create active sites.

The polymerisation catalyst may be a polymerisation catalyst as described in EP2679656A1, paragraphs [0098]-[0107]. The polymerisation catalyst may be a polymerisation catalyst as described in US2010/0331502A1, paragraphs [0067]-[0091], and/or Example 1. The polymerisation catalyst may be a polymerisation catalyst as described in WO2016/023973A1, paragraphs [0045]-[0055].

The properties of the polymers formed in a catalytic polymerisation treatment, such as molecular weight, molecular weight distribution, long chain branching content, density, viscosity, crystallinity, amorphous content, shear thinning behaviour, other rheological parameters, composition distribution indicators such as comonomer distribution breadth index (CDBI), comonomer distribution constant (CDC), thermal stability, melting temperature, crystallisation temperature, melt flow rate (MFR) and others, may be influenced by selection of the catalyst type or catalysts types (as hybrid versions are available and it is possible to feed two or more different catalysts to one or more reactors), the comonomer type, comonomer content, additional monomer (s) and their type and amount(s).

After the polymerisation process, the formed polymers may be further modified to form polymer material. The formed polymers may be modified via one or more extrusion or compounding steps where additional ingredients are optionally added. Such additional ingredients are, for example, stabilisation additives, impact modifiers such as plastomers or elastomers, other blend components in general, fillers such as talc's, glass fibres, carbon fibres, nano-clays or other nanomaterials, carbon black, nucleating agents (which are also possible to add in-situ during the polymerisation treatment or preparation of a polymerisation catalyst), UV stabilisers, pigments, crosslinking or visbreaking agents such as organic peroxides, acid scavengers such as calcium stearate, polymer processing aids for example fluoropolymers. Additional comonomers or functional groups, such as silanes and/or maleic anhydride, may optionally be added to the formed polymers after the polymerisation treatment via reactive extrusion. The formed polymers may after the polymerisation treatment be subjected to further processing steps in conversion. These optional modifications enable production of at least partially bio-based (renewable) versions of the full spectrum of fossil based polymer materials, particularly PE and/or PP materials, and other materials and articles derived from these polymer materials.

The polymers formed in the polymerisation treatment, or the polymer material derived from the formed polymers as described above, may be converted or formed to final parts or products by multiple processes such as extrusion processes for film, sheet, fibres, pipe, profiles, wires and cables, injection moulding processes, hot melt spinning, blow moulding or extrusion blow moulding processes, rotational moulding processes, hot dip coating, calendaring, compacting, chemical and/or physical foaming processes or others. The polymer material derived from the polymers formed in the polymerisation treatment may be used as a direct substitute for fossil based polymer materials in these conversion processes. The polymer material derived from the polymers formed in the polymerisation treatment may optionally be blended with other types of polymers, fillers, additives, or combinations thereof and may optionally be included in composite materials or multilayer structures with other materials, such as other polymer materials, for example fossil based polypropylene, polyvinylidene chloride, polyesters, ethylene vinyl alcohol, aluminium, etc.

The final parts or products described above may be used in a variety of applications. For example, said final parts or products may be used in packaging applications including food and non-food packaging, flexible packaging, heat seal, thin wall packaging, transparent packaging, packaging of dangerous goods, packaging for detergents and personal care, packaging of surfactants, etc. Said final parts or products may be used in consumer goods applications such as caps and closures, toys, bottles, watering cans, white goods and appliances, engineering parts, crates, cartridges, leisure products, housewares, panels and profiles, lids, shoe insoles, pipe clamps, car boot/trunk lining, brushes, corks, ink cartridges, flippers, brushes, collector trays for perforators, seals, hand grips, garden furniture, houseware, thin walled injection moulded parts, co-injection moulded parts, food containers, reusable containers, luggage, ice cream containers, dairy products containers, drinking cups, high impact containers, high stiffness containers, DVD boxes, etc. Said final parts or products may be used in automotive applications, such as parts and assemblies for exterior, interior, under-the-bonnet, bumpers, body panels, trims, facias, dashboards, door claddings, climate control or cooling systems, air intake manifolds or battery cases, instrument panels or soft touch controls, airbag covers, roof pillar mouldings, under the hood belt or hoses, weather strips, anti-vibration systems, rocker panels or side moulding, instrument panels, structural parts, etc. Said final parts or products may be used in wire and cable applications, such as insulation, jacketing or semi-conductive materials for extra-high, high and medium voltage energy transmission and distribution in AC or DC, data or communication cables or jacketing, building wires or cables, automotive wires or cables, photovoltaic encapsulants, etc. Said final parts or products may be used in pipe applications such as multilayer pipes, pressure pipes, gas pipes, drinking water pipes, industrial pipes, wastewater or sewage pipes, in-house plumbing or heating, mono or multi-layer onshore or offshore oil or gas pipeline coatings, pressure pipes for sandless bedding, no dig installation pipes, linings and relinings, corrugated industrial pipes, fittings, mechanical-joint compression fittings, solar heat absorbers, etc. Said final parts or products may be used in film applications, such as heavy duty bags, liners, refuse sacks, carrier bags, agricultural films, building or construction films, heavy duty shrink films, collation shrink films, fine shrink films, food packaging fill form seal (FFS) films or bags, packaging films for sanitary articles, freezer films, sanitary films, embossed release films, lamination films, label films, cling films, surface protection films, sealing layers, cereal packaging, silicon coated films, stretch hoods, etc. Said final parts or products may be used in fibre applications, such as non-woven or technical fibres, continuous filament, filament yarn, raffia, tapes, strapping nets, bulk fibres, etc. Other applications wherein said final parts or products may be used in are, for example, extrusion coating, hot melt adhesives, tie-layer adhesives, medical applications, roofing & waterproofing membranes, carpeting, rubberized surfaces, artificial turf, base resin for masterbatches and compounding.

EXAMPLES

Bio-Based Fresh Feed

A triglyceridic feed comprising a mixture of vegetable and animal oils containing about 40 wt.-% of saturated C16 fatty acids, about 50 wt.-% of unsaturated C18 fatty acids, and having a glycerol equivalent content of about 10 wt.-% was first pre-treated to remove elemental impurities by bleaching. After this the pre-treated raw material stream (bio-based fresh feed material) was diluted. The diluted mixture was processed through hydrodeoxygenation (HDO) to produce a hydrotreatment effluent under the conditions specified below. The hydrotreatment effluent was separated and purified to provide a bio-propane composition, and diesel range paraffinic hydrocarbons.

Bleaching

The bio-renewable oil/fat material was bleached using a conventional bleaching protocol. 2000 ppm of citric acid, 0.2 wt.-% of water and 1 wt.-% of bleaching earth were added to the pre-heated bio-renewable oil/fat material, followed by mixing for 20 min at 80° C., dehydrating using reduced pressure, and filtering. Impurity levels in the bleached bio-renewable oil/fat material are presented in the table below.

| Impurity | mg/kg |
| --- | --- |
| Aluminium | 0.01 |
| Calcium | 0.06 |
| Iron | 0.1 |
| Magnesium | 0.02 |
| Nickel | 0.01 |
| Phosphorus | 0.8 |
| Sodium | 0.1 |
| Nitrogen | 36 |

Hydrodeoxygenation—Step (B)

The bleached bio-renewable oil/fat material was diluted by mixing 5 w-parts of bio-based paraffinic hydrocarbons to 1 w-part of the bleached bio-renewable oil/fat material to form a hydrotreatment feed, which was adjusted with DMDS (dimethyl disulfide) to contain 20-100 wt.-ppm of S (calculated as elemental S) and hydrodeoxygenated using a sulphided metal catalyst at a temperature of 285° C., $H_2$ pressure of about 50 bar, and space velocity of about 0.5-1 g/g*h$^{-1}$. The HDO effluent was separated at a temperature of about 40° C. at the HDO reactor pressure into a gas stream and liquid stream, and water was separated and discarded from the liquid stream to obtain paraffinic hydrocarbons.

Isomerization and Fractionation of the Liquid Stream

The paraffinic hydrocarbons were subjected to a hydroisomerization using conventional platinum-based isomerization catalyst and conventional process conditions. The obtained isoparaffinic hydrocarbon material was directed to fractionation. Diesel range hydrocarbon material meeting EN 590 requirements for automotive diesel fuel was recovered in an amount corresponding to about 83 wt-% of the bio-based fresh feed material.

Purification of the Gas Stream—Step (D)

The propane rich gas stream was first subjected to amine wash (Step (D)) under the following conditions:

amine flow vs. gas flow, 5.8 t/h amine solution per ton sour gas, aqueous amine solution is 50 wt % methyl diethyl amine (MDEA), containing 400 ppm piperazine to enhance $CO_2$ absorption in an absorber a treatment pressure of 4 MPa, gas inlet temperature: about 40° C., amine inlet temperature: about 60° C.

The resulting sweet gas was then passed across a hydrogen selective membrane (Step (E)). The propane rich retentate was then dried (Step (E)) to remove water before the propane product was separated in an elevated pressure distillator at 30 barg and 50° C. to provide a propane feed, which was subsequently compressed to liquid form.

The above procedure from bio-based fresh feed to purified bio-propane was repeated several times varying the feed composition, including the glycerol-equivalent content, feed sulphur level, HDO temperature and $H_2$ pressure, and the separation and purification parameters, while each time operating according to the inventive method, and obtaining bio-propane compositions having the desired characteristics.

Mean analysis results of the resulting bio-propane compositions are shown in table A below, as well as of the inventive bio-propane sample that was used in the dehydrogenation tests below.

TABLE A

Mean analysis results of bio-propane compositions

| Property | Unit | Method | Mean | Bio-propane sample used in the dehy tests |
|---|---|---|---|---|
| C5 + HEAVIER | wt-% | UOP539 | 0.34 | 0.54 |
| CO2 | wt-% | UOP539 | 0.07 | <0.05 |
| CO | wt-% | UOP539 | <0.05 | <0.05 |
| DENSITY | kg/m³ | ENISO8973 | 507 | 508 |
| PROPANE | wt-% | UOP539 | 96.5 | 95.6 |
| SULPHUR | mg/kg | ASTMD6667 | 1.72 | 2.00 |
| Unsaturated Hydrocarbons | wt-% | UOP539 | <0.1 | <0.05 |
| Vapour pressure (40° C.) | kPa | ENISO8973 | 1390 | 1380 |

Catalytic Dehydrogenation

Propane samples used in the dehydrogenation tests included a standard fossil propane composition, a reference bio-propane composition, and a bio-propane composition according to the invention. The bio-propane composition according to the invention was prepared using the above procedure. The reference bio-propane composition was representative of bio-propane prepared using otherwise similar procedure, but starting from a bio-renewable oil/fat material having a lower glycerol equivalent content, and using decarb-favoring conditions in the HDO step (incl. higher temperature, lower $H_2$ pressure).

A Sn-modified Pt catalyst known in the art (such as one prepared according to US 2003/0191351 A1) was used in the dehydrogenation experiments. Alternatively a Cr based catalyst could have been used e.g. as prepared according to US 2015/259265 A1.

The experiments were carried out in a quartz fixed bed reactor with an inner diameter of 2.66 cm and a thermocouple pocket of 4 mm in diameter. The reactor was placed in a three-zone furnace and the lines before and after the reactor as well as the bypass line were heated to 200° C. The bio-propane composition was fed from a gas cylinder via mass flow controllers to the system with additional 5 vol-% of N2 as an internal standard. For liquid feed the gas cylinder was pressurized with N2 and pumped with either a mass flow controller or HPLC pump.

The catalyst was diluted with 5 times the catalyst mass of SiC (e.g., for 5 g of catalyst 25 g of SiC). A 2 cm layer of SiC was added on top of the catalyst bed corresponding to SiC mass of 19 g.

The following procedure was used:

1. Reduction of catalyst system at 550° C. with 50% $H_2$ in $N_2$ for 2 hours
2. N2 flush and change oven temperature to reaction temperature of 575° C.
3. 30 min reaction at 575° C.
4. N2 flush and change oven to regeneration temperature of 600° C. for at least 30 min
5. Regeneration with 1.5% of $O_2$ in N2 for 15 min at 600° C.
6. N2 flush and change oven T for at least 15 min Steps 3 to 6 were repeated four times to evaluate the catalyst deactivation between the first run (dehy_1) and the final run (dehy_4). The overall Experiment was repeated three times per setup to give a standard deviation. The results are shown in Table C below.

The propane rich feed composition to the dehydrogenation reactor was analysed as follows:

Noble gases were measured on a micro-GC: Varian CP-4900, TCD, Channel 1 ($H_2$, $N_2$, $CH_4$, CO): 105° C., carrier gas Ar, column MSSA, Channel 2 ($CO_2$, $C_2H_4$, $C_2H_6$): 80° C., carrier gas He, column PPU, Channel 3 (C3 and C4 compounds): 80° C., carrier gas He, column $Al_2O_3$.

Hydrocarbon composition on the following GC: Shimadzu GC2010 Plus, FID, column Rt-Alumina BOND/MAPD, program, carrier gas He, program: 70° C. 2 min-4° C./min-140° C.-10° C./min-230° C. 9 min.

Sulfur compounds on the following equipment: Agilent 7890B, FPD, column GS Gaspro, carrier gas He, program: 100° C. 2.5 min-15° C./min-220° C. 15 min.

Molar flows and elemental balances were calculated based on the GC results with following equations:

$$Q_{out} = \frac{Q_{in} * x_{N_2,in}}{x_{N_2,out}}$$

$$n_i = \frac{Q * x_i}{V_m}$$

$$X_{propane} = \frac{n_{propane,in} - n_{propane,out}}{n_{propane,in}} * 100$$

$$Y_i = \frac{n_i}{n_{i,in}}$$

Where Q is total volume flow (mol/dm³), $x_i$ is volume fraction of compound i measured with micro-GC, $V_m$ is the molar volume of the gas (dm³/mol), ni is the molar flow of the compound i (mol/min), $X_i$ is conversion and Y, is yield.

The amount of carbon formed in the regeneration was calculated based on the gas analyser results, the $CO_2$ concentration was calculated to carbon flow by following equation:

$$\dot{m}_{C,t} = \frac{(x_{CO_2,t} - x_{CO_2,0}) * Q * M_C}{V_m}$$

The carbon flow was then summed over the measuring interval:

$$m_C = \sum \frac{(m_{C,1} + m_{C,2})/2}{t_2 - t_1}$$

The feed to the reactor was analysed always before starting the experiment. In addition the feedstocks were analysed for minor hydrocarbon compounds separately with GC/FID. In all the analyses propane concentration was calculated by reducing the other compounds from 100%. The permanent gases were analysed with μ-GC.

TABLE B

Compositions of fossil propane, reference bio-propane and inventive bio-propane composition

| | Fossil propane | Reference Bio-propane | Inventive Bio-propane |
|---|---|---|---|
| Analysis of minor hydrocarbons with GC/FID | | | |
| Sulfur (mg/kg) | 18 | 0 | 0 |
| C4's (vol ppm) | 27845 | 7804 | 10231 |
| C5 + (vol ppm) | 7 | 104 | 3076 |
| Unsaturates (vol ppm) | 1895 | 459 | 486 |
| dienes/alkynes (vol ppm) | 2 | 0 | 0 |
| Hydrocarbon composition at inlet as measured by GC | | | |
| CH4 (vol-%) | 0 ± 0 | 1.74 ± 0.26 | 0.06 ± 0.05 |
| CO (vol-%) | 0 ± 0 | 0.26 ± 0.06 | 0 ± 0 |
| CO2 (vol-%) | 0 ± 0 | 0.54 ± 0.03 | 0.06 ± 0.03 |
| C2H6 (vol-%) | 0.71 ± 0.18 | 4.84 ± 0.04 | 1.56 ± 0.25 |
| C2H4 (vol-%) | 0 ± 0 | 0 ± 0 | 0 ± 0 |
| H2 (vol-%) | 0 ± 0 | 0.86 ± 0.33 | 0.01 ± 0 |
| iC4H10 (vol-%) | 2.63 ± 0.19 | 0.36 ± 0.01 | 1.04 ± 0.11 |
| nC4H10 (vol-%) | 0.33 ± 0.08 | 0.35 ± 0.01 | 1.29 ± 0.05 |
| N2 (vol-%, internal standard) | 6.95 ± 0.44 | 8.93 ± 0.75 | 7.28 ± 0.67 |
| O2 (vol-%) | 0.01 ± 0.01 | 0.01 ± 0.02 | 0.01 ± 0.01 |
| C3H8 (vol-%) | 88.74 ± 0.62 | 82.05 ± 1.56 | 88.69 ± 0.69 |
| C3H6 (vol-%) | 0.33 ± 0.05 | 0 ± 0 | 0 ± 0.01 |

As can be seen from Table B, both bio-samples exhibited lower sulfur, C4's and unsaturates contents, in particular less C3H6, while fossil propane exhibited lower C5+ and ethane contents. Main difference between the inventive and the reference bio-propane was that the latter contained CO, and a higher ratio of CO and $CO_2$ to propane.

TABLE C

Conversion and coking results from catalytic dehydrogenation of fossil propane, reference bio-propane and the inventive bio-propane composition.

| | Fossil propane | Reference Bio-propane | Inventive Bio-propane |
|---|---|---|---|
| Propane Conversion (%) | | | |
| dehy_1 | 11.72 ± 6.44 | 25.42 ± 11.1 | 20.98 ± 6.31 |
| dehy_2 | | 16.59 ± 8.56 | 15.17 ± 6.24 |
| dehy_3 | 3.16 ± 3.7 | 9.01 ± 6.74 | 12.46 ± 6.96 |
| dehy_4 | 3.61 ± 2.51 | 7.17 ± 6.24 | 12.78 ± 2.98 |
| Specific Coke (g Coke formed per 1 g C fed over 1 g catalyst × $10^{-9}$) | | | |
| dehy_1 | 130.29 | 198.62 ± 20.31 | 133.07 ± 16.35 |
| dehy_2 | 48.86 | 132.36 ± 30.22 | 86.57 ± 4.33 |
| dehy_3 | 32.57 | 99.25 ± 19.54 | 81.15 ± 22.59 |
| dehy_4 | 32.57 | 86.06 ± 11.56 | 89.04 |
| Characteristics | High: S; | Low: S; | Low: S; |

TABLE C-continued

Conversion and coking results from catalytic dehydrogenation of fossil propane, reference bio-propane and the inventive bio-propane composition.

| | Fossil propane | Reference Bio-propane | Inventive Bio-propane |
|---|---|---|---|
| of the propane | unsaturates Low: CO & CO2 & C5+ | unsaturates High: CO & CO2 Moderate: C5+ | unsaturates Low: CO & CO2 Moderate: C5+ |

As can be seen from Table C dehydrogenation catalyst coking results, the reference bio-propane composition formed most specific coke on the dehydrogenation catalyst. It is assumed that the higher coking tendency is due to the higher CO and $CO_2$ contents compared to the inventive bio-propane composition. On the other hand the fossil propane having higher sulfur content deactivated the catalyst quicker resulting in significantly lower propane to propylene conversion-% compared to both bio-propane samples, but especially compared to the inventive bio-propane. In general, it can be observed that the inactivation of the catalyst (i.e. lower conversion from dehy_1 to dehy_4) similarly results in lower specific coke values. Actually, when normalized over propane conversion (not shown in Table B), the specific coke formation for the inventive sample is superior over the fossil sample.

While the exact role of unsaturates (e.g. olefins and diolefins) and C5+ hydrocarbons (C5 and heavier) was not analysed in detail, the high unsaturates content in fossil propane, including presence of C3H6, may have contributed to the quicker deactivation of the catalyst thus resulting to the lower conversion-%. Unsaturates are highly reactive, and easily undergo unwanted side and secondary reactions, that may affect e.g. the structure and composition of the formed coke, and even lead into formation of so-called hard coke. Surprisingly the higher C5+ contents of the bio-propanes did not reduce the conversion-% that much, potentially reflecting formation of a coke structure/composition that is easier to remove during catalyst regeneration.

The invention claimed is:

1. A method for upgrading a bio-based material, comprising:

(A) providing a bio-based fresh feed material of bio-renewable oils and/or fats having a glycerol-equivalent content of 2 wt.-% to 60 wt.-% relative to a total weight of the bio-based fresh feed material, wherein the bio-renewable oil(s) and/or fat(s) in the bio-based fresh feed material have been pretreated to reduce contaminants in the bio-based fresh feed material;

(B) subjecting a hydrotreatment feed including the bio-based fresh feed material and an optional diluent to a hydrotreatment that includes a presence of a sulphided metal catalyst and hydrogen (H2), to provide a hydrotreated effluent, wherein the hydrotreatment feed includes 10-10 000 wt.-ppm of sulphur-containing (S-containing) compounds calculated as elemental S;

(C) subjecting the hydrotreated effluent to gas-liquid separation so as to provide a gaseous hydrotreated material including H2, bio-propane, H2O, H2S, CO2, and CO, and a liquid hydrotreated material including paraffinic hydrocarbons;

(D) subjecting the liquid hydrotreated material to fractionation, after an optional second hydrotreatment, and recovering at least diesel and/or a kerosene range paraffinic hydrocarbon material;

(E) subjecting the gaseous hydrotreated material to a purification step for removing H2S and CO2 to obtain a H2S and CO2 depleted gaseous stream;

(F) subjecting the H2S and CO2 depleted gaseous stream to H2 recovering and drying to obtain dried H2S, CO2 and H2 depleted gaseous stream;

(G) fractionating and compressing the dried H2S, CO2 and H2 depleted gaseous stream to recover a liquefied bio-propane composition that contains at most 15 wt.-ppm of S-containing compounds, calculated as elemental S.

2. The method according to claim 1, wherein the bio-based fresh feed material has a glycerol-equivalent content of at least 3 wt. %; and/or the bio-based fresh feed material has a glycerol-equivalent content of 55 wt. % or less.

3. The method according to claim 1, wherein the hydrotreatment feed comprises 10-1000 wt.-ppm of S-containing compounds calculated as elemental S.

4. The method according to claim 1, wherein (D) comprises:

subjecting the liquid hydrotreated material to fractionation after a second hydrotreatment including hydroisomerization, and recovering at least diesel and/or a kerosene range iso-paraffinic hydrocarbon material.

5. The method according to claim 1, wherein (E) comprises:

(E') recovering the H2S removed from the gaseous hydrotreated material and recycling the recovered H2S to the hydrotreatment feed.

6. The method according to claim 1, wherein the liquefied bio-propane composition has a propane content of at least 90 wt.-%.

7. The method according to claim 1, comprising:

subjecting at least part of the liquefied bio-propane composition to a conversion including catalytic dehydrogenation to obtain a dehydrogenation effluent, followed by recovering at least bio-propylene in the dehydrogenation effluent to obtain, after optional purification, a bio-propylene composition.

8. The method according to claim 7, comprising:

(co) polymerizing at least bio-propylene of the bio-propylene composition and/or at least a derivative of bio-propylene of the bio-propylene composition, optionally together with other (co) monomer(s), to produce a bio-polymer.

9. The method according to claim 1, wherein the liquefied bio-propane composition possesses a vapour pressure of 1200-1500 kPa at 40° C. and a density of 495-520 kg/m3 at 15° C., and includes:

at least 94 wt.-% of bio-propane;

at most 2000 wt.-ppm of CO2;

at most 1000 wt.-ppm of CO;

at most 1500 wt.-ppm of unsaturated hydrocarbons;

at most 5.5 wt.-% of hydrocarbons having more than 3 carbon atoms (C3+ hydrocarbons), whereof at most 1.4 wt.-% (relative to the liquefied bio-propane composition) are hydrocarbons having 5 or more carbon atoms and optionally at most 1500 wt.-ppm, at most 1000 wt.-ppm, at most 800 wt.-ppm, or at most 500 wt.-ppm of propylene.

10. The method according to claim 1, wherein the bio-based fresh feed material of bio-renewable oils and/or fats has a glycerol-equivalent content of 6 wt.-% to 40 wt.-% relative to a total weight of the bio-based fresh feed material.

11. The method according to claim 1, wherein the hydrotreatment feed includes 10-500 wt.-ppm of sulphur-containing (S-containing) compounds calculated as elemental S.

12. The method according to claim 1, comprising one or more of:

recovering the H2S removed from the gaseous hydrotreated material in step (E) and recycling the recovered H2S to the hydrotreatment feed; and/or subjecting the hydrotreatment feed in step (B) and the diluent to the hydrotreatment of step (B).

* * * * *